US009382555B2

(12) United States Patent
Margeot et al.

(10) Patent No.: US 9,382,555 B2
(45) Date of Patent: Jul. 5, 2016

(54) POLYPETIDE WITH ENHANCED BETA-GLUCOSIDASE ACTIVITY AT LOW TEMPERATURE

(71) Applicants: IFP ENERGIES NOUVELLES, Reuil Malmaison (FR); PROTEUS, Longjumeau (FR); CENTRE NATIONAL DE LA RECHERCHE SCIENTIFIQUE-CNRS, Paris (FR)

(72) Inventors: Antoine Margeot, Paris (FR); Hugues Mathis, Bussy Saint Georges (FR); Celine Ayrinhac, Domessargues (FR); Christophe Ullmann, Nimes (FR); Cecile Persillon, Nimes (FR); Sebastien Fort, Uriage (FR); Sylvie Armand, Grenoble (FR); Maud Petit, La Tronche (FR)

(73) Assignees: IFP ENERGIES NOUVELLES, Rueil Malmaison (FR); PROTÉUS, Longjumeau (FR); CENTRE NATIONAL DE LA RECHERCHE SCIENTIFIQUE-CNRS, Paris (FR)

(*) Notice: Subject to any disclaimer, the term of this patent is extended or adjusted under 35 U.S.C. 154(b) by 0 days.

(21) Appl. No.: 14/425,175

(22) PCT Filed: Sep. 4, 2013

(86) PCT No.: PCT/FR2013/052036
§ 371 (c)(1),
(2) Date: Mar. 2, 2015

(87) PCT Pub. No.: WO2014/037667
PCT Pub. Date: Mar. 13, 2014

(65) Prior Publication Data
US 2015/0218593 A1  Aug. 6, 2015

(30) Foreign Application Priority Data
Sep. 5, 2012 (FR) ..................... 12 58260

(51) Int. Cl.
*C12N 9/24* (2006.01)
*C12N 15/52* (2006.01)
*C12N 15/09* (2006.01)
*C12N 1/15* (2006.01)
*C12N 1/21* (2006.01)
*C12P 7/06* (2006.01)
*C12P 7/16* (2006.01)
*C12P 19/02* (2006.01)
*C12P 7/14* (2006.01)
*C12P 19/14* (2006.01)
*C12N 9/42* (2006.01)
*C12P 7/10* (2006.01)

(52) U.S. Cl.
CPC ................ *C12P 7/14* (2013.01); *C12N 9/2437* (2013.01); *C12N 9/2445* (2013.01); *C12P 7/10* (2013.01); *C12P 19/02* (2013.01); *C12P 19/14* (2013.01); *C12P 2203/00* (2013.01); *Y02E 50/16* (2013.01); *Y02P 20/52* (2015.11)

(58) Field of Classification Search
None
See application file for complete search history.

(56) References Cited

U.S. PATENT DOCUMENTS

2010/0304438 A1  12/2010  Scott et al.
2011/0171674 A1*  7/2011  Lopes-Ferreira ......... C12P 7/04
                                                                435/18

FOREIGN PATENT DOCUMENTS

WO        92/10581 A1    6/1992
WO    2010/029259 A1    3/2010
WO    2010/148148 A2   12/2010

OTHER PUBLICATIONS

Dashtban, Mehdi et al., "Fungal Bioconversion of Lignocellulosic Residues; Opportunities & Perspectives" International Journal of Biological Sciences (2009), vol. 5(6), pp. 578-595.
Ayrinhac, Celine et al., "Improved Saccharifiation of Wheat Straw for Biofuel Production Using an Engineered Secretome of Trichoderma reesei" Organic Process Research & Development (2011), vol. 15, pp. 275-278.
International Search Report and Written Opinion of PCT/FR2013/052036 dated Nov. 13, 2013.

* cited by examiner

*Primary Examiner* — David J Steadman
(74) *Attorney, Agent, or Firm* — McDonnell Boehnen Hulbert & Berghoff

(57) ABSTRACT

The invention relates to a polypeptide which has enhanced beta-glucosidase activity at a temperature of between about 30° C. and about 35° C.

16 Claims, No Drawings

SEQUENCE LISTING

<160> NUMBER OF SEQ ID NOS: 12

<210> SEQ ID NO 1
<211> LENGTH: 744
<212> TYPE: PRT
<213> ORGANISM: Trichoderma atraviride

```
<400> SEQUENCE: 1

Met Arg Tyr Arg Thr Ala Ala Ala Leu Ala Leu Ala Thr Gly Pro Phe
1               5                   10                  15

Ala Arg Ala Asp Ser His Ser Thr Ser Gly Ala Ser Ala Glu Ala Val
            20                  25                  30

Val Pro Pro Ala Gly Thr Pro Trp Gly Thr Ala Tyr Asp Lys Ala Lys
            35                  40                  45

Ala Ala Leu Ala Lys Leu Leu Gln Asp Lys Val Gly Ile Val Ser
    50                  55                  60

Gly Val Gly Trp Asn Gly Gly Pro Cys Val Gly Asn Thr Ser Pro Ala
65                  70                  75                  80

Ser Lys Ile Gly Tyr Pro Gln Leu Cys Leu Gln Asp Gly Pro Leu Gly
                85                  90                  95

Ile Arg Phe Gly Gly Ser Val Thr Ala Phe Thr Pro Gly Ile Gln Ala
                100                 105                 110

Ala Ser Thr Trp Asp Thr Glu Leu Met Arg Gln Arg Gly Glu Tyr Leu
                115                 120                 125

Gly Ala Glu Ala Lys Gly Cys Gly Ile His Val Leu Leu Gly Pro Val
130                 135                 140

Ala Gly Pro Leu Gly Lys Thr Pro Gln Gly Gly Arg Asn Trp Glu Gly
145                 150                 155                 160

Phe Gly Val Asp Pro Tyr Leu Thr Gly Ile Ala Met Ala Glu Thr Ile
                165                 170                 175

Glu Gly Leu Gln Ser Ala Gly Val Gln Ala Cys Ala Lys His Tyr Ile
                180                 185                 190

Val Asn Glu Gln Glu Leu Asn Arg Glu Thr Ile Ser Ser Asn Pro Asp
                195                 200                 205

Asp Arg Thr Leu His Glu Leu Tyr Leu Trp Pro Phe Ala Asp Ala Val
                210                 215                 220

His Ala Asn Val Ala Ser Val Met Cys Ser Tyr Asn Lys Ile Asn Gly
225                 230                 235                 240

Ser Trp Ala Cys Glu Asp Gln Tyr Thr Leu Gln Thr Val Leu Lys Asp
                245                 250                 255

Gln Leu Gly Phe Pro Gly Tyr Val Met Thr Asp Trp Asn Ala Gln His
                260                 265                 270

Thr Thr Val Gln Ser Ala Asn Ser Gly Leu Asp Met Ser Met Pro Gly
                275                 280                 285

Thr Asp Phe Asn Gly Asn Asn Arg Leu Trp Gly Pro Ala Leu Thr Asn
                290                 295                 300

Ala Val Asn Ser Asn Gln Val Pro Thr Ser Arg Val Asp Asp Met Val
305                 310                 315                 320

Thr Arg Ile Leu Ala Ala Trp Tyr Leu Thr Gly Gln Asp Gln Ala Gly
                325                 330                 335

Tyr Pro Ser Phe Asn Ile Ser Arg Asn Val Gln Gly Asn His Lys Thr
                340                 345                 350

Asn Val Arg Ala Ile Ala Arg Asp Gly Ile Val Leu Leu Lys Asn Asp
                355                 360                 365

Ala Asn Ile Leu Pro Leu Lys Lys Pro Ala Ser Ile Ala Val Val Gly
                370                 375                 380

Ser Ala Ala Ile Ile Gly Asn His Ala Arg Asn Ser Pro Ser Cys Asn
385                 390                 395                 400

Asp Lys Gly Cys Asp Asp Gly Ala Leu Gly Met Gly Trp Gly Ser Gly
```

```
                405                 410                 415
Ala Val Asn Tyr Pro Tyr Phe Val Ala Pro Tyr Asp Ala Ile Asn Thr
            420                 425                 430

Arg Ala Ser Ser Gln Gly Thr Gln Val Thr Leu Ser Asn Thr Asp Asn
            435                 440                 445

Thr Ser Ser Gly Ala Ser Ala Ala Arg Gly Lys Asp Val Ala Ile Val
450                 455                 460

Phe Ile Thr Ala Asp Ser Gly Glu Gly Tyr Ile Thr Val Glu Gly Asn
465                 470                 475                 480

Ala Gly Asp Arg Asn Asn Leu Asp Pro Trp His Asn Gly Asn Ala Leu
            485                 490                 495

Val Gln Ala Val Ala Gly Ala Asn Ser Asn Val Ile Val Val Val His
            500                 505                 510

Ser Val Gly Ala Ile Ile Leu Glu Gln Ile Leu Ala Leu Pro Gln Val
            515                 520                 525

Lys Ala Val Val Trp Ala Gly Leu Pro Ser Gln Glu Ser Gly Asn Ala
530                 535                 540

Leu Val Asp Val Leu Trp Gly Asp Val Ser Pro Ser Gly Lys Leu Val
545                 550                 555                 560

Tyr Thr Ile Ala Lys Ser Pro Asn Asp Tyr Asn Thr Arg Ile Val Ser
            565                 570                 575

Gly Gly Ser Asp Ser Phe Ser Glu Gly Leu Phe Ile Asp Tyr Lys His
            580                 585                 590

Phe Asp Asp Ala Asn Ile Thr Pro Arg Tyr Glu Phe Gly Tyr Gly Leu
            595                 600                 605

Ser Tyr Thr Lys Phe Asn Tyr Ser Arg Leu Ser Val Leu Ser Thr Ala
            610                 615                 620

Lys Ser Gly Pro Ala Thr Gly Ala Val Val Pro Gly Gly Pro Ser Asp
625                 630                 635                 640

Leu Phe Gln Asn Val Ala Thr Val Thr Val Asp Ile Ala Asn Ser Gly
            645                 650                 655

Gln Val Thr Gly Ala Glu Val Ala Gln Leu Tyr Ile Thr Tyr Pro Ser
            660                 665                 670

Ser Ala Pro Arg Thr Pro Lys Gln Leu Arg Gly Phe Ala Lys Leu
            675                 680                 685

Asn Leu Thr Pro Gly Gln Ser Gly Thr Ala Thr Phe Asn Ile Arg Arg
            690                 695                 700

Arg Asp Leu Ser Tyr Trp Asp Thr Ala Ser Gln Lys Trp Val Val Pro
705                 710                 715                 720

Ser Gly Ser Phe Gly Ile Ser Val Gly Ala Ser Ser Arg Asp Ile Arg
            725                 730                 735

Leu Thr Ser Thr Leu Ser Val Ala
            740

<210> SEQ ID NO 2
<211> LENGTH: 2235
<212> TYPE: DNA
<213> ORGANISM: Trichoderma atraviride

<400> SEQUENCE: 2
atgcgttacc gaacagcagc tgcgctggca cttgccactg ggcccttttgc tagggcagac    60 agtcactcaa catcgggggc ctcggctgag gcagttgtac ctcctgcagg gactccatgg   120
ggaaccgcgt acgacaaggc gaaggccgca ttggcaaagc tcaatctcca agataaggtc   180
```

| | |
|---|---|
| ggcatcgtga gcggtgtcgg ctggaacggc ggtccttgcg ttggaaacac atctccggcc | 240 |
| tccaagatcg gctatccaca gctatgcctt caagacggac ccctcggtat ccgattcggc | 300 |
| ggcagcgtca cagcctttac gccgggcatc caagcggcct cgacgtggga taccgagttg | 360 |
| atgcgccagc gtggagagta cctgggtgcc gaggccaagg gctgcgggat tcatgtcctg | 420 |
| cttggtcctg tggctgggcc gctgggaaag actccgcagg gcggtcgcaa ctgggagggc | 480 |
| ttcggtgtcg atccatatct cacgggcatt gccatggccg agacaatcga gggcctgcag | 540 |
| tcggccggcg tgcaggcgtg cgcgaagcac tatatcgtca acgagcagga gctcaatcga | 600 |
| gaaaccattt cgagcaaccc agatgaccga actctccatg agctgtatct gtggccattt | 660 |
| gccgacgcgg ttcacgccaa tgtcgcttct gtcatgtgct cgtacaacaa gatcaatggc | 720 |
| agctgggcct gcgaggatca gtacacgctg cagactgtgc tgaaagacca gctggggttc | 780 |
| ccaggctatg tcatgacgga ctggaacgca cagcacacga ctgtccaaag cgcgaattct | 840 |
| gggcttgaca tgtcaatgcc tggcacagac ttcaacggta caatcggct ctggggtcca | 900 |
| gctctcacca atgcggtaaa tagcaatcag gtccccacga gcagagtcga cgatatggtg | 960 |
| actcgtatcc tcgccgcatg gtacttgaca ggccaggacc aggcaggcta tccgtcgttc | 1020 |
| aacatcagca gaaatgttca aggaaaccac aagaccaatg tcagggcaat tgccagggac | 1080 |
| ggcatcgttc tgctcaagaa tgacgccaac atcctgccgc tcaagaagcc cgctagcatt | 1140 |
| gccgtcgttg gatctgccgc aatcattggt aaccacgcca gaaactcgcc ctcgtgcaac | 1200 |
| gacaaaggct gcgacgacgg ggccttgggc atgggttggg gttccggcgc cgtcaactat | 1260 |
| ccgtacttcg tcgcgcccta cgatgccatc aataccagag cgtcttcgca gggcacccag | 1320 |
| gttaccttga gcaacaccga caacacgtcc tcaggcgcat ctgcagcaag aggaaaggac | 1380 |
| gtcgccatcg tcttcatcac cgccgactcg ggtgaaggct acatcaccgt ggagggcaac | 1440 |
| gcgggcgatc gcaacaacct ggatccgtgg cacaacggca atgccctggt ccaggcggtg | 1500 |
| gccggtgcca cagcaacgt cattgttgtt gtccactccg ttggcgccat cattctggag | 1560 |
| cagattcttg ctcttccgca ggtcaaggcc gttgtctggg cgggtcttcc ttctcaggag | 1620 |
| agcggcaatg cgctcgtcga cgtgctgtgg ggagatgtca gcccttctgg caagctggtg | 1680 |
| tacaccattg cgaagagccc caatgactat aacactcgca tcgtttccgg cggcagtgac | 1740 |
| agcttcagcg agggactgtt catcgactat aagcacttcg acgacgccaa tatcacgccg | 1800 |
| cggtacgagt tcggctatgg actgtcttac accaagttca actactcacg cctctccgtc | 1860 |
| ttgtcgaccg ccaagtctgg tcctgcgact ggggccgttg tgccgggagg cccgagtgat | 1920 |
| ctgttccaga atgtcgcgac agtcaccgtt gacatcgcaa actctggcca agtgactggt | 1980 |
| gccgaggtag cccagctgta catcacctac ccatcttcag cacccaggac ccctccgaag | 2040 |
| cagctgcgag gctttgccaa gctgaacctc acgcctggtc agagcggaac agcaacgttc | 2100 |
| aacatccgac gacgagatct cagctactgg gacacggctt cgcagaaatg ggtggtgccg | 2160 |
| tcggggtcgt ttggcatcag cgtgggagcg agcagccggg atatcaggct gacgagcact | 2220 |
| ctgtcggtag cgtag | 2235 |

<210> SEQ ID NO 3
<211> LENGTH: 744
<212> TYPE: PRT
<213> ORGANISM: Trichoderma atraviride

<400> SEQUENCE: 3

Met Arg Tyr Arg Thr Ala Ala Ala Leu Ala Leu Ala Thr Gly Pro Phe

```
1               5                   10                  15
Ala Arg Ala Asp Ser His Ser Thr Ser Gly Ala Ser Ala Glu Ala Val
                20                  25                  30

Val Pro Pro Ala Gly Thr Pro Trp Gly Thr Ala Tyr Asp Lys Ala Lys
                35                  40                  45

Ala Ala Leu Ala Lys Leu Asn Leu Gln Asp Lys Val Gly Ile Val Ser
 50                  55                  60

Gly Val Gly Trp Asn Gly Gly Pro Cys Val Gly Asn Thr Ser Pro Ala
 65                  70                  75                  80

Ser Lys Ile Ser Tyr Pro Ser Leu Cys Leu Gln Asp Gly Pro Leu Gly
                    85                  90                  95

Val Arg Tyr Ser Thr Gly Ser Thr Ala Phe Thr Pro Gly Val Gln Ala
                100                 105                 110

Ala Ser Thr Trp Asp Val Asn Leu Ile Arg Glu Arg Gly Gln Phe Ile
                115                 120                 125

Gly Glu Glu Val Lys Ala Ser Gly Ile His Val Ile Leu Gly Pro Val
            130                 135                 140

Ala Gly Pro Leu Gly Lys Thr Pro Gln Gly Gly Arg Asn Trp Glu Gly
145                 150                 155                 160

Phe Gly Val Asp Pro Tyr Leu Thr Gly Ile Ala Met Gly Gln Thr Ile
                    165                 170                 175

Asn Gly Ile Gln Ser Val Gly Val Gln Ala Thr Ala Lys His Tyr Ile
                180                 185                 190

Leu Asn Glu Gln Glu Leu Asn Arg Glu Thr Ile Ser Ser Asn Pro Asp
                195                 200                 205

Asp Arg Thr Leu His Glu Leu Tyr Thr Trp Pro Phe Ala Asp Ala Val
            210                 215                 220

Gln Ala Asn Val Ala Ser Val Met Cys Ser Tyr Asn Lys Val Asn Thr
225                 230                 235                 240

Thr Trp Ala Cys Glu Asp Gln Tyr Thr Leu Gln Thr Val Leu Lys Asp
                    245                 250                 255

Gln Leu Gly Phe Pro Gly Tyr Val Met Thr Asp Trp Asn Ala Gln His
                260                 265                 270

Thr Thr Val Gln Ser Ala Asn Ser Gly Leu Asp Met Ser Met Pro Gly
            275                 280                 285

Thr Asp Phe Asn Gly Asn Asn Arg Leu Trp Gly Pro Ala Leu Thr Asn
290                 295                 300

Ala Val Asn Ser Asn Gln Val Pro Thr Ser Arg Val Asp Asp Met Val
                    310                 315                 320

Thr Arg Ile Leu Ala Ala Trp Tyr Leu Thr Gly Gln Asp Gln Ala Gly
                325                 330                 335

Tyr Pro Ser Phe Asn Ile Ser Arg Asn Val Gln Gly Asn His Lys Thr
                340                 345                 350

Asn Val Arg Ala Ile Ala Arg Asp Gly Ile Val Leu Leu Lys Asn Asp
            355                 360                 365

Ala Asn Ile Leu Pro Leu Lys Lys Pro Ala Ser Ile Ala Val Val Gly
370                 375                 380

Ser Ala Ala Ile Ile Gly Asn His Ala Arg Asn Ser Pro Ser Cys Asn
385                 390                 395                 400

Asp Lys Gly Cys Asp Asp Gly Ala Leu Gly Met Gly Trp Gly Ser Gly
                    405                 410                 415

Ala Val Asn Tyr Pro Tyr Phe Val Ala Pro Tyr Asp Ala Ile Asn Thr
                420                 425                 430
```

```
Arg Ala Ser Ser Gln Gly Thr Gln Val Thr Leu Ser Asn Thr Asp Asn
            435                 440                 445

Thr Ser Ser Gly Ala Ser Ala Ala Arg Gly Lys Asp Val Ala Ile Val
        450                 455                 460

Phe Ile Thr Ala Asp Ser Gly Glu Gly Tyr Ile Thr Val Glu Gly Asn
465                 470                 475                 480

Ala Gly Asp Arg Asn Asn Leu Asp Pro Trp His Asn Gly Asn Ala Leu
            485                 490                 495

Val Gln Ala Val Ala Gly Ala Asn Ser Asn Val Ile Val Val Val His
            500                 505                 510

Ser Val Gly Ala Ile Ile Leu Glu Gln Ile Leu Ala Leu Pro Gln Val
            515                 520                 525

Lys Ala Val Val Trp Ala Gly Leu Pro Ser Gln Glu Ser Gly Asn Ala
            530                 535                 540

Leu Val Asp Val Leu Trp Gly Asp Val Ser Pro Ser Gly Lys Leu Val
545                 550                 555                 560

Tyr Thr Ile Ala Lys Ser Pro Asn Asp Tyr Asn Thr Arg Ile Val Ser
            565                 570                 575

Gly Gly Ser Asp Ser Phe Ser Glu Gly Leu Phe Ile Asp Tyr Lys His
            580                 585                 590

Phe Asp Asp Ala Asn Ile Thr Pro Arg Tyr Glu Phe Gly Tyr Gly Leu
            595                 600                 605

Ser Tyr Thr Lys Phe Asn Tyr Ser Arg Leu Ser Val Leu Ser Thr Ala
            610                 615                 620

Lys Ser Gly Pro Ala Thr Gly Ala Val Val Pro Gly Gly Pro Ser Asp
625                 630                 635                 640

Leu Phe Gln Asn Val Ala Thr Val Thr Val Asp Ile Ala Asn Ser Gly
            645                 650                 655

Gln Val Thr Gly Ala Glu Val Ala Gln Leu Tyr Ile Thr Tyr Pro Ser
            660                 665                 670

Ser Ala Pro Arg Thr Pro Pro Lys Gln Leu Arg Gly Phe Ala Lys Leu
            675                 680                 685

Asn Leu Thr Pro Gly Gln Ser Gly Thr Ala Thr Phe Asn Ile Arg Arg
            690                 695                 700

Arg Asp Leu Ser Tyr Trp Asp Thr Ala Ser Gln Lys Trp Val Val Pro
705                 710                 715                 720

Ser Gly Ser Phe Gly Ile Ser Val Gly Ala Ser Ser Arg Asp Ile Arg
            725                 730                 735

Leu Thr Ser Thr Leu Ser Val Ala
            740

<210> SEQ ID NO 4
<211> LENGTH: 2235
<212> TYPE: DNA
<213> ORGANISM: Trichoderma reesei

<400> SEQUENCE: 4
atgcgttacc gaacagcagc tgcgctggca cttgccactg ggcccttttgc tagggcagac      60 agtcactcaa catcggggc ctcggctgag gcagttgtac ctcctgcagg gactccatgg      120
ggaaccgcgt acgacaaggc gaaggccgca ttggcaaagc tcaatctcca agataaggtc      180
ggcatcgtga cgcgtgtcgg ctggaacggg gtccttgcg ttggaaacac atctccggcc      240
tccaagatca gctatccatc gctatgcctt caagacggac ccctcggtgt tcgatactcg      300
```

| | |
|---|---|
| acaggcagca cagcctttac gccgggcgtt caagcggcct cgacgtggga tgtcaatttg | 360 |
| atccgcgaac gtggacagtt catcggtgag gaggtgaagg cctcgggat tcatgtcata | 420 |
| cttggtcctg tggctgggcc gctgggaaag actccgcagg gcggtcgcaa ctgggagggc | 480 |
| ttcggtgtcg atccatatct cacgggcatt gccatgggtc aaaccatcaa cggcatccag | 540 |
| tcggtaggcg tgcaggcgac agcgaagcac tatatcctca cgagcagga gctcaatcga | 600 |
| gaaaccattt cgagcaaccc agatgaccga actctccatg agctgtatac ttggccatt | 660 |
| gccgacgcgg ttcaggccaa tgtcgcttct gtcatgtgct cgtacaacaa ggtcaatacc | 720 |
| acctgggcct gcgaggatca gtacacgctg cagactgtgc tgaaagacca gctggggttc | 780 |
| ccaggctatg tcatgacgga ctggaacgca cagcacacga ctgtccaaag cgcgaattct | 840 |
| gggcttgaca tgtcaatgcc tggcacagac ttcaacggta caatcggct ctggggtcca | 900 |
| gctctcacca atgcggtaaa tagcaatcag gtccccacga gcagagtcga cgatatggtg | 960 |
| actcgtatcc tcgccgcatg gtacttgaca ggccaggacc aggcaggcta tccgtcgttc | 1020 |
| aacatcagca gaaatgttca aggaaaccac aagaccaatg tcagggcaat tgccagggac | 1080 |
| ggcatcgttc tgctcaagaa tgacgccaac atcctgccgc tcaagaagcc cgctagcatt | 1140 |
| gccgtcgttg atctgccgc aatcattggt aaccacgcca gaaactcgcc ctcgtgcaac | 1200 |
| gacaaaggct gcgacgacgg ggccttgggc atgggttggg gttccggcgc cgtcaactat | 1260 |
| ccgtacttcg tcgcgcccta cgatgccatc aataccagag cgtcttcgca gggcacccag | 1320 |
| gttaccttga gcaacaccga caacacgtcc tcaggcgcat ctgcagcaag aggaaaggac | 1380 |
| gtcgccatcg tcttcatcac cgccgactcg ggtgaaggct acatcaccgt ggagggcaac | 1440 |
| gcgggcgatc gcaacaacct ggatccgtgg cacaacggca atgccctggt ccaggcggtg | 1500 |
| gccggtgcca acagcaacgt cattgttgtt gtccactccg ttggcgccat cattctggag | 1560 |
| cagattcttg ctcttccgca ggtcaaggcc gttgtctggg cgggtcttcc ttctcaggag | 1620 |
| agcggcaatg cgctcgtcga cgtgctgtgg ggagatgtca gcccttctgg caagctggtg | 1680 |
| tacaccattg cgaagagccc caatgactat aacactcgca tcgtttccgg cggcagtgac | 1740 |
| agcttcagcg agggactgtt catcgactat aagcacttcg acgacgccaa tatcacgccg | 1800 |
| cggtacgagt tcggctatgg actgtcttac accaagttca actactcacg cctctccgtc | 1860 |
| ttgtcgaccg ccaagtctgg tcctgcgact ggggccgttg tgccgggagg cccgagtgat | 1920 |
| ctgttccaga atgtcgcgac agtcaccgtt gacatcgcaa actctggcca agtgactggt | 1980 |
| gccgaggtag cccagctgta catcacctac ccatcttcag cacccaggac ccctccgaag | 2040 |
| cagctgcgag gctttgccaa gctgaacctc acgcctggtc agagcggaac agcaacgttc | 2100 |
| aacatccgac gacgagatct cagctactgg gacacggctt cgcagaaatg ggtggtgccg | 2160 |
| tcggggtcgt ttggcatcag cgtgggagcg agcagccggg atatcaggct gacgagcact | 2220 |
| ctgtcggtag cgtag | 2235 |

```
<210> SEQ ID NO 5
<211> LENGTH: 744
<212> TYPE: PRT
<213> ORGANISM: Trichoderma reesei

<400> SEQUENCE: 5

Met Arg Tyr Arg Thr Ala Ala Ala Leu Ala Leu Ala Thr Gly Pro Phe
1               5                   10                  15

Ala Arg Ala Asp Ser His Ser Thr Ser Gly Ala Ser Ala Glu Ala Val
            20                  25                  30
```

```
Val Pro Pro Ala Gly Thr Pro Trp Gly Thr Ala Tyr Asp Lys Ala Lys
        35                  40                  45

Ala Ala Leu Ala Lys Leu Asn Leu Gln Asp Lys Val Gly Ile Val Ser
 50                  55                  60

Gly Val Gly Trp Asn Gly Gly Pro Cys Val Gly Asn Thr Ser Pro Ala
 65                  70                  75                  80

Ser Lys Ile Ser Tyr Pro Ser Leu Cys Leu Gln Asp Gly Pro Leu Gly
                 85                  90                  95

Ile Arg Phe Gly Thr Gly Ser Thr Ala Phe Thr Pro Gly Val Gln Ala
                100                 105                 110

Ala Ser Thr Trp Asp Thr Glu Leu Met Arg Gln Arg Gly Glu Tyr Leu
            115                 120                 125

Gly Ala Glu Ala Lys Gly Cys Gly Ile His Val Leu Leu Gly Pro Val
130                 135                 140

Ala Gly Pro Leu Gly Lys Thr Pro Gln Gly Gly Arg Asn Trp Glu Gly
145                 150                 155                 160

Phe Gly Val Asp Pro Tyr Leu Thr Gly Ile Ala Met Ala Glu Thr Ile
                165                 170                 175

Glu Gly Leu Gln Ser Ala Gly Val Gln Ala Cys Ala Lys His Tyr Ile
            180                 185                 190

Val Asn Glu Gln Glu Leu Asn Arg Glu Thr Ile Ser Ser Asp Val Asp
        195                 200                 205

Asp Arg Thr Met His Glu Leu Tyr Leu Trp Pro Phe Ala Asp Ala Val
    210                 215                 220

Gln Ala Asn Val Ala Ser Val Met Cys Ser Tyr Asn Lys Ile Asn Gly
225                 230                 235                 240

Ser Trp Ala Cys Glu Asp Gln Tyr Thr Leu Gln Thr Val Leu Lys Asp
                245                 250                 255

Gln Leu Gly Phe Pro Gly Tyr Val Met Thr Asp Trp Asn Ala Gln His
            260                 265                 270

Thr Thr Val Gln Ser Ala Asn Ser Gly Leu Asp Met Ser Met Pro Gly
        275                 280                 285

Thr Asp Phe Asn Gly Asn Asn Arg Leu Trp Gly Pro Ala Leu Thr Asn
    290                 295                 300

Ala Val Asn Ser Asn Gln Val Pro Thr Ser Arg Val Asp Asp Met Val
305                 310                 315                 320

Thr Arg Ile Leu Ala Ala Trp Tyr Leu Thr Gly Gln Asp Gln Ala Gly
                325                 330                 335

Tyr Pro Ser Phe Asn Ile Ser Arg Asn Val Gln Gly Asn His Lys Thr
            340                 345                 350

Asn Val Arg Ala Ile Ala Arg Asp Gly Ile Val Leu Leu Lys Asn Asp
        355                 360                 365

Ala Asn Ile Leu Pro Leu Lys Lys Pro Ala Ser Ile Ala Val Val Gly
370                 375                 380

Ser Ala Ala Ile Ile Gly Asn His Ala Arg Asn Ser Pro Ser Cys Asn
385                 390                 395                 400

Asp Lys Gly Cys Asp Asp Gly Ala Leu Gly Met Gly Trp Gly Ser Gly
                405                 410                 415

Ala Val Asn Tyr Pro Tyr Phe Val Ala Pro Tyr Asp Ala Ile Asn Thr
            420                 425                 430

Arg Ala Ser Ser Gln Gly Thr Gln Val Thr Leu Ser Asn Thr Asp Asn
        435                 440                 445
```

```
Thr Ser Ser Gly Ala Ser Ala Ala Arg Gly Lys Asp Val Ala Ile Val
            450                 455                 460

Phe Ile Thr Ala Asp Ser Gly Glu Gly Tyr Ile Thr Val Glu Gly Asn
465                 470                 475                 480

Ala Gly Asp Arg Asn Asn Leu Asp Pro Trp His Asn Gly Asn Ala Leu
                485                 490                 495

Val Gln Ala Val Ala Gly Ala Asn Ser Asn Val Ile Val Val His
            500                 505                 510

Ser Val Gly Ala Ile Ile Leu Glu Gln Ile Leu Ala Leu Pro Gln Val
            515                 520                 525

Lys Ala Val Val Trp Ala Gly Leu Pro Ser Gln Glu Ser Gly Asn Ala
530                 535                 540

Leu Val Asp Val Leu Trp Gly Asp Val Ser Pro Ser Gly Lys Leu Val
545                 550                 555                 560

Tyr Thr Ile Ala Lys Ser Pro Asn Asp Tyr Asn Thr Arg Ile Val Ser
                565                 570                 575

Gly Gly Ser Asp Ser Phe Ser Glu Gly Leu Phe Ile Asp Tyr Lys His
                580                 585                 590

Phe Asp Asp Ala Asn Ile Thr Pro Arg Tyr Glu Phe Gly Tyr Gly Leu
                595                 600                 605

Ser Tyr Thr Lys Phe Asn Tyr Ser Arg Leu Ser Val Phe Ser Thr Ala
            610                 615                 620

Lys Ser Gly Pro Ala Thr Gly Ala Val Val Pro Gly Gly Pro Ser Asp
625                 630                 635                 640

Leu Phe Gln Asn Val Ala Thr Val Thr Val Asp Ile Ala Asn Ser Gly
                645                 650                 655

Gln Val Thr Gly Ala Glu Val Ala Gln Leu Tyr Ile Thr Tyr Pro Ser
            660                 665                 670

Ser Ala Pro Arg Thr Pro Pro Lys Gln Leu Arg Gly Phe Ala Lys Leu
            675                 680                 685

Asn Leu Thr Pro Gly Gln Ser Gly Thr Ala Thr Phe Asn Ile Arg Arg
690                 695                 700

Arg Asp Leu Ser Tyr Trp Asp Thr Ala Ser Gln Lys Trp Val Val Pro
705                 710                 715                 720

Ser Gly Ser Phe Gly Ile Ser Val Gly Ala Ser Ser Arg Asp Ile Arg
                725                 730                 735

Leu Thr Ser Thr Leu Ser Val Ala
            740

<210> SEQ ID NO 6
<211> LENGTH: 2235
<212> TYPE: DNA
<213> ORGANISM: Trichoderma reesei

<400> SEQUENCE: 6
atgcgttacc gaacagcagc tgcgctggca cttgccactg ggccctttgc tagggcagac      60
agtcactcaa catcgggggc ctcggctgag gcagttgtac ctcctgcagg gactccatgg     120
ggaaccgcgt acgacaaggc gaaggccgca ttggcaaagc tcaatctcca agataaggtc     180
ggcatcgtga gcggtgtcgg ctggaacggg gtccttgcg ttggaaacac atctccggcc     240
tccaagatca gctatccatc gctatgcctt caagacggac ccctcggtat ccgattcggc     300
acaggcagca cagcctttac gccgggcgtt caagcggcct cgacgtggga taccgagttg     360
atgcgccagc gtggagagta cctgggtgcc gaggccaagg gctgcgggat tcatgtcctg     420
```

-continued

```
cttggtcctg tggctgggcc gctgggaaag actccgcagg gcggtcgcaa ctgggagggc    480
ttcggtgtcg atccatatct cacgggcatt gccatggccg agacaatcga gggcctgcag    540
tcggccggcg tgcaggcgtg cgcgaagcac tatatcgtca acgagcagga gctcaatcga    600
gaaaccattt cgagcgacgt cgatgaccga actatgcatg agctgtatct gtggccattt    660
gccgacgcgg ttcaggccaa tgtcgcttct gtcatgtgct cgtacaacaa gatcaatggc    720
agctgggcct gcgaggatca gtacacgctg cagactgtgc tgaaagacca gctgggttc    780
ccaggctatg tcatgacgga ctggaacgca cagcacacga ctgtccaaag cgcgaattct    840
gggcttgaca tgtcaatgcc tggcacagac ttcaacggta caatcggct ctggggtcca    900
gctctcacca atgcggtaaa tagcaatcag gtccccacga gcagagtcga cgatatggtg    960
actcgtatcc tcgccgcatg gtacttgaca ggccaggacc aggcaggcta tccgtcgttc   1020
aacatcagca gaaatgttca aggaaaccac aagaccaatg tcagggcaat tgccagggac   1080
ggcatcgttc tgctcaagaa tgacgccaac atcctgccgc tcaagaagcc cgctagcatt   1140
gccgtcgttg atctgccgc aatcattggt aaccacgcca gaaactcgcc ctcgtgcaac   1200
gacaaaggct gcgacgacgg ggccttgggc atgggttggg gttccggcgc cgtcaactat   1260
ccgtacttcg tcgcgcccta cgatgccatc aataccagag cgtcttcgca gggcacccag   1320
gttaccttga gcaacaccga caacacgtcc tcaggcgcat ctgcagcaag aggaaaggac   1380
gtcgccatcg tcttcatcac cgccgactcg ggtgaaggct acatcaccgt ggagggcaac   1440
gcgggcgatc gcaacaacct ggatccgtgg cacaacggca atgccctggt ccaggcggtg   1500
gccggtgcca acagcaacgt cattgttgtt gtccactccg ttggcgccat cattctggag   1560
cagattcttg ctcttccgca ggtcaaggcc gttgtctggg cgggtcttcc ttctcaggag   1620
agcggcaatg cgctcgtcga cgtgctgtgg ggagatgtca gcccttctgg caagctggtg   1680
tacaccattg cgaagagccc caatgactat aacactcgca tcgtttccgg cggcagtgac   1740
agcttcagcg agggactgtt catcgactat aagcacttcg acgacgccaa tatcacgccg   1800
cggtacgagt tcggctatgg actgtcttac accaagttca actactcacg cctctccgtc   1860
ttttcgaccg ccaagtctgg tcctgcgact ggggccgttg tgccgggagg cccgagtgat   1920
ctgttccaga atgtcgcgac agtcaccgtt gacatcgcaa actctggcca agtgactggt   1980
gccgaggtag cccagctgta catcacctac ccatcttcag cacccaggac ccctccgaag   2040
cagctgcgag gctttgccaa gctgaacctc acgcctggtc agagcggaac agcaacgttc   2100
aacatccgac gacgagatct cagctactgg gacacggctt cgcagaaatg ggtggtgccg   2160
tcggggtcgt ttggcatcag cgtgggagcg agcagccggg atatcaggct gacgagcact   2220
ctgtcggtag cgtag                                                    2235
```

<210> SEQ ID NO 7
<211> LENGTH: 726
<212> TYPE: PRT
<213> ORGANISM: Chaetomium globosum

<400> SEQUENCE: 7

Met Thr Thr Leu Arg Asn Phe Ala Leu Leu Ala Ala Val Leu Ala
1               5                   10                  15

Arg Val Glu Ala Leu Glu Ala Ala Asp Trp Ala Ala Ala Glu Ala Ser
            20                  25                  30

Ala Lys Thr Ala Leu Ala Lys Met Ser Gln Gln Asp Lys Ile Ser Ile
        35                  40                  45

-continued

Val Thr Gly Ile Gly Trp Asp Lys Gly Pro Cys Val Gly Asn Thr Ala
 50                  55                  60

Ala Ile Asn Ser Ile Asn Tyr Pro Gln Leu Cys Leu Gln Asp Gly Pro
 65                  70                  75                  80

Leu Gly Ile Arg Phe Gly Thr Gly Ser Thr Ala Phe Thr Pro Gly Val
                 85                  90                  95

Gln Ala Ala Ser Thr Trp Asp Thr Glu Leu Met Arg Gln Arg Gly Glu
                100                 105                 110

Tyr Leu Gly Ala Glu Ala Lys Gly Cys Gly Ile His Val Leu Leu Gly
            115                 120                 125

Pro Val Ala Gly Ala Leu Gly Lys Ile Pro His Gly Gly Arg Asn Trp
130                 135                 140

Glu Gly Phe Gly Thr Asp Pro Tyr Leu Ala Gly Ile Ala Met Ala Glu
145                 150                 155                 160

Thr Ile Glu Gly Leu Gln Ser Ala Gly Val Gln Ala Cys Ala Lys His
                165                 170                 175

Tyr Ile Val Asn Glu Gln Glu Leu Asn Arg Glu Thr Ile Ser Ser Asp
            180                 185                 190

Val Asp Asp Arg Thr Met His Glu Leu Tyr Leu Trp Pro Phe Ala Asp
            195                 200                 205

Ala Val His Ala Asn Val Ala Ser Val Met Cys Ser Tyr Asn Lys Ile
210                 215                 220

Asn Gly Ser Trp Gly Cys Glu Asn Asp His Ala Gln Asn Gly Leu Leu
225                 230                 235                 240

Lys Lys Glu Leu Gly Phe Lys Gly Tyr Val Val Ser Asp Trp Asn Ala
                245                 250                 255

Gln His Thr Thr Asp Gly Ala Ala Asn Asn Gly Met Asp Met Thr Met
            260                 265                 270

Pro Gly Ser Asp Tyr Asn Gly Asn Asn Val Leu Trp Gly Pro Gln Leu
            275                 280                 285

Ser Asn Ala Val Asn Ser Asn Arg Val Ser Arg Asp Arg Leu Asp Asp
290                 295                 300

Met Ala Lys Arg Ile Leu Thr Ser Trp Tyr Leu Leu Gly Gln Asn Ser
305                 310                 315                 320

Gly Tyr Pro Asn Ile Asn Ile Asn Ala Asn Val Gln Gly Asn His Lys
                325                 330                 335

Glu Asn Val Arg Ala Val Ala Arg Asp Gly Ile Val Leu Leu Lys Asn
            340                 345                 350

Asp Glu Gly Val Leu Pro Leu Lys Lys Pro Gly Lys Val Ala Leu Val
            355                 360                 365

Gly Ser Ala Ala Ser Val Asn Ser Ala Gly Pro Asn Ala Cys Val Asp
370                 375                 380

Lys Gly Cys Asn Thr Gly Ala Leu Gly Met Gly Trp Gly Ser Gly Ser
385                 390                 395                 400

Val Asn Tyr Pro Tyr Phe Val Ala Pro Tyr Asp Ala Leu Lys Thr Arg
                405                 410                 415

Ala Gln Ala Asp Gly Thr Thr Leu Ser Leu His Asn Ser Asp Ser Thr
            420                 425                 430

Asn Gly Val Ser Gly Val Ser Gly Ala Asp Val Ala Ile Val Val
            435                 440                 445

Ile Thr Ala Asp Ser Gly Glu Gly Tyr Ile Thr Val Glu Gly His Ala
450                 455                 460

Gly Asp Arg Asn His Leu Asp Pro Trp His Asp Gly Asn Ala Leu Val

```
                465                 470                 475                 480
Lys Ala Val Ala Ala Asn Lys Asn Thr Ile Val Val His Ser
                    485                 490                 495

Thr Gly Pro Ile Ile Leu Glu Thr Ile Leu Ala Thr Glu Gly Val Lys
            500                 505                 510

Ala Val Val Trp Ala Gly Leu Pro Ser Gln Glu Asn Gly Asn Ala Leu
            515                 520                 525

Val Asp Val Leu Tyr Gly Leu Thr Ser Pro Ser Gly Lys Leu Val Tyr
        530                 535                 540

Ser Ile Ala Lys Arg Pro Glu Asp Tyr Gly Thr Ala Pro Ser Lys Gly
545                 550                 555                 560

Ser Asn Asp Lys Phe Thr Glu Gly Leu Phe Val Asp Tyr Arg His Phe
                565                 570                 575

Asp Asn Ala Lys Ile Glu Pro Arg Tyr Glu Phe Gly Phe Gly Leu Ser
            580                 585                 590

Tyr Thr Glu Phe Thr Tyr Ala Asp Leu Ser Val Thr Ser Thr Val Thr
        595                 600                 605

Ala Gly Pro Ala Ser Gly Glu Thr Ile Pro Gly Gly Ala Ala Asp Leu
    610                 615                 620

Trp Glu Thr Val Ala Thr Val Thr Ala Ser Ile Thr Asn Ser Gly Glu
625                 630                 635                 640

Val Glu Gly Ala Glu Val Ala Gln Leu Tyr Ile Thr Leu Pro Ser Ala
                645                 650                 655

Ala Pro Ser Thr Pro Pro Lys Gln Leu Arg Gly Phe Ala Lys Leu Lys
            660                 665                 670

Leu Glu Pro Gly Ala Ser Gly Val Ala Thr Phe Asn Leu Arg Arg Arg
        675                 680                 685

Asp Leu Ser Tyr Trp Asp Ala Gly Arg Gly Gln Trp Val Val Pro Ala
    690                 695                 700

Gly Glu Phe Thr Val Ser Val Gly Ala Ser Ser Arg Asp Val Arg Leu
705                 710                 715                 720

Thr Gly Ser Leu Thr Ala
            725

<210> SEQ ID NO 8
<211> LENGTH: 2181
<212> TYPE: DNA
<213> ORGANISM: Chaetomium globosum

<400> SEQUENCE: 8
atgacgacgc tccgcaactt tgcgctgctc gcagcggcgg tgcttgcgcg ggtcgaggcc      60
ctcgaggccg ccgactgggc tgcggctgag gcctcagcca aaaccgcact ggcaaagatg     120
tcacaacaag acaaaatcag cattgtgacg ggcatcggct gggacaaggg tccctgtgtc     180
ggcaacacgg ccgccatcaa ctcgatcaac tacccgcagc tctgcctaca ggacggcccg     240
ctcgggatcc gcttcggcac cggctcgacg gccttcaccc cggcgtccca agccgcctcg     300
acatgggata ccgagctgat cgccagcgc ggcgagtacc tcggggccga ggccaagggg     360
tgcggcatcc acgtgttgct gggccccgtg gccgggcac tggcaagat cccgcacggc     420 gggcgcaact gggaaggatt cgggacggac ccgtacctgg cgggcatcgc catggccgag     480
acgatcgagg gctgcagtc ggcgggggtg caggcgtgcg ccaagcacta catcgtcaac     540
gagcaggagc tcaaccgcga gaccatcagc agcgacgtcg acgaccgcac catgcacgag     600
ctgtacctgt ggcccttcgc cgacgccgtg cacgccaacg tggccagcgt catgtgcagc     660
```

```
tacaacaaga tcaacggctc gtggggctgc gagaacgacc acgcccaaaa cggcctgctc    720
aagaaggagc tcggcttcaa gggttacgtc gtcagcgact ggaacgcgca gcacacgacc    780
gacggcgccg ccaacaacgg catggacatg accatgccgg gcagcgacta caacggcaac    840
aacgtgctct ggggcccgca gctcagcaac gccgtcaaca gcaacggggt ctcgcgcgac    900
cggctcgacg acatggccaa acgcatcctc acctcatggt acctcctggg ccagaactcg    960
ggctacccca acatcaacat caacgccaac gtgcagggca accacaagga gaacgtgcgg   1020
gcggtggcgc gcgacggcat cgtgctgctc aagaacgacg agggcgtgct cccgctgaag   1080
aagccaggca aggtggctct cgtcggatcg cggcctcgg tcaacagcgc gggccccaac    1140
gcgtgcgtcg acaagggctg caacacgggc gcgctcggca tgggctgggg gtccgggtcc   1200
gtcaactacc cctactttgt ggcgccctac gacgcgctca agacgcgcgc ccaggccgac   1260
ggcaccacgc tcagcctgca caactcggac tcgaccaacg gcgtatcggg cgtggtgtcg   1320
ggcgccgacg tggccatcgt ggtgatcacg gcggactcgg gcgagggcta catcacggtc   1380
gagggccacg ccggcgaccg caaccacctg gacccgtggc acgacggcaa cgcgctggtt   1440
aaggcggtgg ccgcggccaa caagaacacc atcgtggtag tgcacagcac agggcccatc   1500
atcctcgaga ccatcctggc gacggagggt gtcaaggcgg ttgtgtgggc cggcctgccg   1560
agtcaggaga cggcaacgc gctagttgac gttttgtacg gcctgacttc gccctcaggc    1620
aaactggtct actccatcgc caagcgcccc gaggactatg gcacggcccc ctccaagggc   1680
agtaacgaca agttcaccga aggcctgttt gtcgactacc ggcactttga caacgccaag   1740
attgagccgc ggtacgagtt tggctttggt ttgtcctaca ccgaattcac ctacgccgac   1800
ctctccgtca cttccaccgt aacggccggc cccgcctcag gcgagaccat cccggcggc    1860
gcggccgacc tctgggagac tgtcgcaacg gtcacggcgt ccatcacgaa cagcggcgag   1920
gtggagggcg ccgaggtggc gcagctgtac atcacgctgc cgtcggcggc ccctcgacg    1980
ccgcccaagc agctgcgcgg gttcgccaag ctcaagctcg agccgggggc gtcgggcgtc   2040
gcgaccttca acctgcgccg tcgcgatctg agttattggg atgccgggcg cggccagtgg   2100
gtggtgccgg cgggcgagtt tacggtttcg gttggtgcga gttcgaggga tgtgcgcttg   2160
acggggagct tgactgctta g                                             2181
```

<210> SEQ ID NO 9
<211> LENGTH: 735
<212> TYPE: PRT
<213> ORGANISM: Neurospora crassa

<400> SEQUENCE: 9

Met His Leu Arg Ile Phe Ala Val Leu Ala Ala Thr Ser Leu Ala Trp
1               5                   10                  15

Ala Glu Thr Ser Glu Lys Gln Ala Arg Gln Ala Gly Ser Gly Phe Ala
            20                  25                  30

Ala Trp Asp Ala Ala Tyr Ser Gln Ala Ser Thr Ala Leu Ser Lys Leu
        35                  40                  45

Ser Gln Gln Asp Lys Val Asn Ile Val Thr Gly Val Gly Trp Asn Lys
    50                  55                  60

Gly Pro Cys Val Gly Asn Thr Pro Ala Ile Ala Ser Ile Gly Tyr Pro
65                  70                  75                  80

Gln Leu Cys Leu Gln Asp Gly Pro Leu Gly Ile Arg Phe Gly Gly Ser
                85                  90                  95

Val Thr Ala Phe Thr Pro Gly Ile Gln Ala Ala Ser Thr Trp Asp Val
            100                 105                 110

Glu Leu Ile Arg Gln Arg Gly Val Tyr Leu Gly Ala Glu Ala Arg Gly
            115                 120                 125

Val Gly Val His Val Leu Leu Gly Pro Val Ala Gly Ala Leu Gly Lys
            130                 135                 140

Ile Pro Asn Gly Gly Arg Asn Trp Glu Gly Phe Gly Pro Asp Pro Tyr
145                 150                 155                 160

Leu Thr Gly Ile Ala Met Ser Glu Thr Ile Glu Gly Ile Gln Ser Asn
                165                 170                 175

Gly Val Gln Ala Cys Ala Lys His Phe Ile Leu Asn Glu Gln Glu Thr
            180                 185                 190

Asn Arg Asp Thr Ile Ser Ser Val Val Asp Asp Arg Thr Met His Glu
            195                 200                 205

Leu Tyr Leu Phe Pro Phe Ala Asp Ala Val His Ser Asn Val Ala Ser
            210                 215                 220

Val Met Cys Ser Tyr Asn Lys Val Asn Gly Thr Trp Ala Cys Glu Asn
225                 230                 235                 240

Asp Lys Ile Gln Asn Gly Leu Leu Lys Lys Glu Leu Gly Phe Lys Gly
                245                 250                 255

Tyr Val Met Ser Asp Trp Asn Ala Gln His Thr Thr Asn Gly Ala Ala
            260                 265                 270

Asn Ser Gly Met Asp Met Thr Met Pro Gly Ser Asp Phe Asn Gly Lys
            275                 280                 285

Thr Ile Leu Trp Gly Pro Gln Leu Asn Thr Ala Val Asn Asn Gly Gln
290                 295                 300

Val Ser Lys Ala Arg Leu Asp Asp Met Ala Lys Arg Ile Leu Ala Ser
305                 310                 315                 320

Trp Tyr Leu Leu Glu Gln Asn Ser Gly Tyr Pro Ala Thr Asn Leu Lys
                325                 330                 335

Ala Asn Val Gln Gly Asn His Lys Glu Asn Val Arg Ala Val Ala Arg
            340                 345                 350

Asp Gly Ile Val Leu Leu Lys Asn Asp Asp Asn Ile Leu Pro Leu Lys
            355                 360                 365

Lys Pro Ser Lys Leu Ala Ile Ile Gly Ser Ser Val Val Asn Pro
            370                 375                 380

Ala Gly Arg Asn Ala Cys Thr Asp Arg Gly Cys Asn Thr Gly Ala Leu
385                 390                 395                 400

Gly Met Gly Trp Gly Ser Gly Thr Ala Asp Tyr Pro Tyr Phe Val Ala
                405                 410                 415

Pro Tyr Asp Ala Leu Lys Thr Arg Ala Gln Ser Asp Gly Thr Thr Val
            420                 425                 430

Asn Leu Leu Ser Ser Asp Ser Thr Ser Gly Val Ala Asn Ala Ala Ser
            435                 440                 445

Gly Ala Asp Ala Ala Leu Val Phe Ile Thr Ala Asp Ser Gly Glu Gly
            450                 455                 460

Tyr Ile Thr Val Glu Gly Val Thr Gly Asp Arg Pro Asn Leu Asp Pro
465                 470                 475                 480

Trp His Asn Gly Asn Gln Leu Val Gln Ala Val Ala Gln Ala Asn Lys
                485                 490                 495

Asn Thr Ile Val Val Val His Ser Thr Gly Pro Ile Ile Leu Glu Thr
            500                 505                 510

Ile Leu Ala Gln Pro Gly Val Lys Ala Val Val Trp Ala Gly Leu Pro

```
                   515                 520                 525
Ser Gln Glu Asn Gly Asn Ala Leu Val Asp Val Leu Tyr Gly Leu Val
        530                 535                 540

Ser Pro Ser Gly Lys Leu Pro Tyr Thr Ile Ala Lys Ser Glu Ser Asp
545                 550                 555                 560

Tyr Gly Thr Ala Val Gln Arg Gly Gly Thr Asp Leu Phe Thr Glu Gly
                565                 570                 575

Leu Phe Ile Asp Tyr Arg His Phe Asp Lys Asn Gly Ile Ala Pro Arg
            580                 585                 590

Tyr Glu Phe Gly Phe Gly Leu Ser Tyr Thr Asn Phe Thr Tyr Ser Ser
        595                 600                 605

Leu Ser Ile Thr Ser Thr Ala Ser Ser Gly Pro Ala Ser Gly Asp Thr
    610                 615                 620

Ile Pro Gly Gly Arg Ala Asp Leu Trp Glu Thr Val Ala Thr Val Thr
625                 630                 635                 640

Ala Val Val Lys Asn Thr Gly Gly Val Gln Gly Ala Glu Ala Pro Gln
                645                 650                 655

Leu Tyr Ile Thr Leu Pro Ser Ser Ala Pro Ser Ser Pro Pro Lys Gln
            660                 665                 670

Leu Arg Gly Phe Ala Lys Leu Lys Leu Ala Pro Gly Glu Ser Lys Thr
        675                 680                 685

Ala Thr Phe Ile Leu Arg Arg Arg Asp Leu Ser Tyr Trp Asp Thr Gly
    690                 695                 700

Ser Gln Asn Trp Val Val Pro Ser Gly Ser Phe Gly Val Val Val Gly
705                 710                 715                 720

Ala Ser Ser Arg Asp Leu Arg Leu Asn Gly Lys Phe Asp Val Tyr
                725                 730                 735

<210> SEQ ID NO 10
<211> LENGTH: 2208
<212> TYPE: DNA
<213> ORGANISM: Neurospora crassa

<400> SEQUENCE: 10
atgcaccttc gaatatttgc ggtgttggcc gcgacttccc tcgcctgggc cgagactagc      60
gagaaacaag ctcgtcaagc tggctcaggt tttgcggcgt gggacgcagc ctattctcag     120
gcaagcactg ctctctccaa gctttcacag caagacaagg tcaacatcgt caccggagtc     180
ggctggaata agggcccatg tgttggcaac accccagcta ttgcatcaat cggttatccc     240
cagctctgtt tacaagacgg ccctctcggc attcggtttg gaggaagtgt caccgcgttc     300
acgcctggta tccaggcggc ttcaacatgg acgtcgaac  tgattcgaca gcgcggcgtc     360
tacctcggtg cagaagccag aggggttggc gtacatgtcc ttcttggacc cgtggccgga     420
gcgcttggca agatccccaa tggtggacgt aactgggagg ctttggtcc  ggatccctac     480 ctcacaggta ttgccatgag cgaaacaatt gaagggatcc agagcaatgg tgtacaagct     540
tgcgccaagc acttcattct caacgaacag gagacaaacc gcgatactat cagcagtgtc     600
gtcgacgacc gcaccatgca tgaactatac ctcttccctt ttgccgatgc cgtacactca     660
aatgttgcaa gtgtgatgtg cagctacaac aaggtcaacg tacgtgggc  atgtgagaat     720 gacaaaatcc agaatggcct tctcaagaaa gagctaggct caaaggata  tgtcatgagt     780 gattggaacg cccagcacac cacgaacggc gctgcaaaca gtggtatgga tatgacgatg     840
ccaggcagtg actttaatgg caagacgatc ctgtggggac acagctcaa  caccgccgtc     900
```

```
aacaatggcc aggtctccaa agcaagactg gacgacatgg ccaagcgcat tctcgcatcg    960
tggtatttac tcgagcaaaa ctcaggctac cctgcgacta acctcaaggc caatgttcaa   1020
ggaaaccaca aggagaacgt tcgcgcagtg caagagacg gcattgttct gctgaagaac    1080
gacgataaca tcctcccgct caagaagcct agcaagctgg caatcattgg gtcatcgtcc   1140
gttgtcaacc ctgcgggaag gaacgcctgc accgatcgag gatgcaacac cggtgcgctc   1200
ggcatgggtt ggggctccgg cacggccgat taccccctact tcgtagcacc ctatgatgct   1260
ctcaagacgc gggctcagtc cgacggaaca actgtcaacc tactcagctc tgacagcacc   1320
agcggcgtag ccaacgctgc ctccggagcc gacgcggcac tagtcttcat cacagccgat   1380
tccggcgaag gctacatcac ggtcgagggc gtgaccggcg accgtcccaa cctcgatccc   1440
tggcacaacg gcaaccagct agtccaagcc gtggctcaag ccaacaagaa caccattgtc   1500
gtcgtccaca gtaccggccc catcattctg gagactatcc tcgcgcagcc gggcgtcaag   1560
gcggtcgtgt gggccggtct ccccagccaa gagaacggca acgcccttgt cgatgtccta   1620
tacggcttgg tctctcccctc gggtaagctg ccgtatacta tcgccaagag cgaaagcgac   1680
tacggcactg ccgtgcaaag gggagggacg gatctgttca ctgagggtct gttcatcgat   1740
taccgccact ttgacaagaa cggtatcgct ccccggtatg agttcggttt cggtctttcc   1800
tacacgaact tcacctactc ctccctctcc atcacctcca ccgcctcctc cggtcccgcc   1860
tcgggtgaca ccatccctgg cggccgcgcc gacctctggg aaaccgtggc aaccgtcact   1920
gccgtcgtca aaaacacggg tggtgtgcag ggcgccgagg caccccagct atacatcacc   1980
ttgcccctctt ccgcgccgtc gagcccgccg aaacagctca gagggtttgc aaagctgaag   2040
ctggcgcccg gggagagcaa gacagctacg ttcattttgc ggaggaggga tttgagttat   2100
tgggatacgg gcagccagaa ttgggtggtg cctagtggca gctttggggt ggtagtgggt   2160
gctagttcga gggatttgag gttgaatggg aagtttgatg tttattga              2208
```

<210> SEQ ID NO 11
<211> LENGTH: 744
<212> TYPE: PRT
<213> ORGANISM: Trichoderma reesei

<400> SEQUENCE: 11

```
Met Arg Tyr Arg Thr Ala Ala Leu Ala Leu Ala Thr Gly Pro Phe
1               5                   10                  15

Ala Arg Ala Asp Ser His Ser Thr Ser Gly Ala Ser Ala Glu Ala Val
            20                  25                  30

Val Pro Pro Ala Gly Thr Pro Trp Gly Thr Ala Tyr Asp Lys Ala Lys
        35                  40                  45

Ala Ala Leu Ala Lys Leu Asn Leu Gln Asp Lys Val Gly Ile Val Ser
    50                  55                  60

Gly Val Gly Trp Asn Gly Gly Pro Cys Val Gly Asn Thr Ser Pro Ala
65                  70                  75                  80

Ser Lys Ile Ser Tyr Pro Ser Leu Cys Leu Gln Asp Gly Pro Leu Gly
                85                  90                  95

Ile Arg Phe Gly Thr Gly Ser Thr Ala Phe Thr Pro Gly Val Gln Ala
            100                 105                 110

Ala Ser Thr Trp Asp Val Asn Leu Ile Arg Glu Arg Gly Gln Phe Ile
        115                 120                 125

Gly Glu Glu Val Lys Ala Ser Gly Ile His Val Ile Leu Gly Pro Val
    130                 135                 140
```

-continued

```
Ala Gly Pro Leu Gly Lys Ile Pro His Gly Arg Asn Trp Glu Gly
145                 150                 155                 160

Phe Gly Val Asp Pro Tyr Leu Thr Gly Ile Ala Met Ala Glu Thr Ile
                165                 170                 175

Glu Gly Leu Gln Ser Ala Gly Val Gln Ala Cys Ala Lys His Tyr Ile
            180                 185                 190

Leu Asn Glu Gln Glu Leu Asn Arg Glu Thr Ile Ser Ser Asn Pro Asp
        195                 200                 205

Asp Arg Thr Leu His Glu Leu Tyr Thr Trp Pro Phe Ala Asp Ala Val
    210                 215                 220

His Ala Asn Val Ala Ser Val Met Cys Ser Tyr Asn Lys Ile Asn Gly
225                 230                 235                 240

Ser Trp Ala Cys Glu Asp Gln Tyr Thr Leu Gln Thr Val Leu Lys Asp
                245                 250                 255

Gln Leu Gly Phe Pro Gly Tyr Val Met Thr Asp Trp Asn Ala Gln His
            260                 265                 270

Thr Thr Val Gln Ser Ala Asn Ser Gly Leu Asp Met Ser Met Pro Gly
        275                 280                 285

Thr Asp Phe Asn Gly Asn Asn Arg Leu Trp Gly Pro Ala Leu Thr Asn
    290                 295                 300

Ala Val Asn Ser Asn Gln Val Pro Thr Ser Arg Val Asp Asp Met Val
305                 310                 315                 320

Thr Arg Ile Leu Ala Ala Trp Tyr Leu Thr Gly Gln Asp Gln Ala Gly
                325                 330                 335

Tyr Pro Ser Phe Asn Ile Ser Arg Asn Val Gln Gly Asn His Lys Thr
            340                 345                 350

Asn Val Arg Ala Ile Ala Arg Asp Gly Ile Val Leu Leu Lys Asn Asp
        355                 360                 365

Ala Asn Ile Leu Pro Leu Lys Lys Pro Ala Ser Ile Ala Val Val Gly
    370                 375                 380

Ser Ala Ala Ile Ile Gly Asn His Ala Arg Asn Ser Pro Ser Cys Asn
385                 390                 395                 400

Asp Lys Gly Cys Asp Asp Gly Ala Leu Gly Met Gly Trp Gly Ser Gly
                405                 410                 415

Ala Val Asn Tyr Pro Tyr Phe Val Ala Pro Tyr Asp Ala Ile Asn Thr
            420                 425                 430

Arg Ala Ser Ser Gln Gly Thr Gln Val Thr Leu Ser Asn Thr Asp Asn
        435                 440                 445

Thr Ser Ser Gly Ala Ser Ala Arg Gly Lys Asp Val Ala Ile Val
    450                 455                 460

Phe Ile Thr Ala Asp Ser Gly Glu Gly Tyr Ile Thr Val Glu Gly Asn
465                 470                 475                 480

Ala Gly Asp Arg Asn Asn Leu Asp Pro Trp His Asn Gly Asn Ala Leu
                485                 490                 495

Val Gln Ala Val Ala Gly Ala Asn Ser Asn Val Ile Val Val His
            500                 505                 510

Ser Val Gly Ala Ile Ile Leu Glu Gln Ile Leu Ala Leu Pro Gln Val
        515                 520                 525

Lys Ala Val Val Trp Ala Gly Leu Pro Ser Gln Glu Ser Gly Asn Ala
    530                 535                 540

Leu Val Asp Val Leu Trp Gly Asp Val Ser Pro Ser Gly Lys Leu Val
545                 550                 555                 560

Tyr Thr Ile Ala Lys Ser Pro Asn Asp Tyr Asn Thr Arg Ile Val Ser
```

```
                565                 570                 575
Gly Gly Ser Asp Ser Phe Ser Glu Gly Leu Phe Ile Asp Tyr Lys His
            580                 585                 590

Phe Asp Asp Ala Asn Ile Thr Pro Arg Tyr Glu Phe Gly Tyr Gly Leu
            595                 600                 605

Ser Tyr Thr Lys Phe Asn Tyr Ser Arg Leu Ser Val Leu Ser Thr Ala
            610                 615                 620

Lys Ser Gly Pro Ala Thr Gly Ala Val Val Pro Gly Gly Pro Ser Asp
625                 630                 635                 640

Leu Phe Gln Asn Val Ala Thr Val Thr Val Asp Ile Ala Asn Ser Gly
            645                 650                 655

Gln Val Thr Gly Ala Glu Val Ala Gln Leu Tyr Ile Thr Tyr Pro Ser
            660                 665                 670

Ser Ala Pro Arg Thr Pro Pro Lys Gln Leu Arg Gly Phe Ala Lys Leu
            675                 680                 685

Asn Leu Thr Pro Gly Gln Ser Gly Thr Ala Thr Phe Asn Ile Arg Arg
            690                 695                 700

Arg Asp Leu Ser Tyr Trp Asp Thr Ala Ser Gln Lys Trp Val Val Pro
705                 710                 715                 720

Ser Gly Ser Phe Gly Ile Ser Val Gly Ala Ser Ser Arg Asp Ile Arg
            725                 730                 735

Leu Thr Ser Thr Leu Ser Val Ala
            740

<210> SEQ ID NO 12
<211> LENGTH: 2235
<212> TYPE: DNA
<213> ORGANISM: Trichoderma reesei

<400> SEQUENCE: 12
atgcgttacc gaacagcagc tgcgctggca cttgccactg ggcccttgc tagggcagac        60 agtcactcaa catcgggggc ctcggctgag gcagttgtac ctcctgcagg gactccatgg      120
ggaaccgcgt acgacaaggc gaaggccgca ttggcaaagc tcaatctcca agataaggtc      180
ggcatcgtga gcggtgtcgg ctggaacggc ggtccttgcg ttggaaacac atctccggcc      240
tccaagatca gctatccatc gctatgcctt caagacggac ccctcggtat ccgattcggc      300
acaggcagca gcctttac gccgggcgtt caagcggcct cgacgtggga tgtcaatttg        360
atccgcgaac gtggacagtt catcggtgag gaggtgaagg cctcggggat tcatgtcata      420
cttggtcctg tggctgggcc gctgggaaag atcccgcacg gcggtcgcaa ctgggagggc      480
ttcggtgtcg atccatatct cacgggcatt gccatggccg agacaatcga gggcctgcag      540
tcggccggcg tgcaggcgtg gcgaagcac tatatcctca acgagcagga gctcaatcga      600
gaaaccattt cgagcaaccc agatgaccga actctccatg agctgtatac ttggccattt      660
gccgacgcgt tcacgccaa tgtcgcttct gtcatgtgct cgtacaacaa gatcaatggc      720
agctgggcct gcgaggatca gtacacgctg cagactgtgc tgaaagacca gctgggggttc      780 ccaggctatg tcatgacgga ctggaacgca cagcacacga ctgtccaaag cgcgaattct      840
gggcttgaca tgtcaatgcc tggcacagac ttcaacggta caatcggct ctggggtcca      900 gctctcacca atgcggtaaa tagcaatcag gtccccacga gcagagtcga cgatatggtg      960
actcgtatcc tcgccgcatg gtacttgaca ggccaggacc aggcaggcta tccgtcgttc     1020
aacatcagca gaaatgttca aggaaaccac aagaccaatg tcagggcaat tgccagggac     1080
```

-continued

```
ggcatcgttc tgctcaagaa tgacgccaac atcctgccgc tcaagaagcc cgctagcatt  1140
gccgtcgttg gatctgccgc aatcattggt aaccacgcca gaaactcgcc ctcgtgcaac  1200
gacaaaggct gcgacgacgg ggccttgggc atgggttggg gttccggcgc cgtcaactat  1260
ccgtacttcg tcgcgcccta cgatgccatc aataccagag cgtcttcgca gggcacccag  1320
gttaccttga gcaacaccga caacacgtcc tcaggcgcat ctgcagcaag aggaaaggac  1380
gtcgccatcg tcttcatcac cgccgactcg ggtgaaggct acatcaccgt ggagggcaac  1440
gcgggcgatc gcaacaacct ggatccgtgg cacaacggca atgccctggt ccaggcggtg  1500
gccggtgcca acagcaacgt cattgttgtt gtccactccg ttggcgccat cattctggag  1560
cagattcttg ctcttccgca ggtcaaggcc gttgtctggg cgggtcttcc ttctcaggag  1620
agcggcaatg cgctcgtcga cgtgctgtgg ggagatgtca gcccttctgg caagctggtg  1680
tacaccattg cgaagagccc caatgactat aacactcgca tcgtttccgg cggcagtgac  1740
agcttcagcg agggactgtt catcgactat aagcacttcg acgacgccaa tatcacgccg  1800
cggtacgagt tcggctatgg actgtcttac accaagttca actactcacg cctctccgtc  1860
ttgtcgaccg ccaagtctgg tcctgcgact ggggccgttg tgccgggagg cccgagtgat  1920
ctgttccaga atgtcgcgac agtcaccgtt gacatcgcaa actctggcca agtgactggt  1980
gccgaggtag cccagctgta catcacctac ccatcttcag cacccaggac ccctccgaag  2040
cagctgcgag gctttgccaa gctgaacctc acgcctggtc agagcggaac agcaacgttc  2100
aacatccgac gacgagatct cagctactgg gacacggctt cgcagaaatg ggtggtgccg  2160
tcggggtcgt ttggcatcag cgtgggagcg agcagccggg atatcaggct gacgagcact  2220
ctgtcggtag cgtag                                                   2235
```

POLYPETIDE WITH ENHANCED BETA-GLUCOSIDASE ACTIVITY AT LOW TEMPERATURE

This application is a U.S. national phase of International Application No. PCT/FR2013/052036, filed Sep. 4, 2013, which claims priority from French application no. FR 1258260, filed Sep. 5, 2012, the disclosure of each of which is hereby incorporated by reference in its entirety.

The possibility of producing ethanol from cellulose has received a great deal of attention owing to the availability of large amounts of raw material and also to the interest in ethanol as a fuel. Cellulose-based natural raw materials for such a process are denoted "biomass". Numerous types of biomass, for example wood, agricultural residues, herbaceous crops and solid urban waste, have been considered as potential raw materials for producing biofuel. These materials consist mainly of cellulose, hemicellulose and lignin.

Cellulose is a polymer consisting of glucose molecules linked by beta-1,4 bonds, which are very resistant to degradation or to depolymerization. Once cellulose has been converted into glucose, the latter is easily fermented to biofuel, for example ethanol, using a yeast.

The oldest methods studied for converting cellulose to glucose are based on acid hydrolysis. This process can be carried out in the presence of concentrated or dilute acids. However, several drawback, such as the poor recovery of the acid when concentrated acids are used and the low production of glucose in the case of the use of dilute acids, are detrimental to the economics of the acid hydrolysis process.

In order to overcome the drawbacks of the acid hydrolysis process, cellulose conversion processes have more recently related to enzymatic hydrolysis, using enzymes of cellulase type. This enzymatic hydrolysis of lignocellulosic biomass (for example, cellulose) has, however, the drawback of being an expensive industrial process. Consequently, it is necessary to use increasingly effective cellulase-secreting microorganism strains. In this respect, many microorganisms comprise enzymes which hydrolyze cellulose, such as the fungi *Trichoderma, Aspergillus, Humicola* or *Fusarium*, and also bacteria such as *Thermomonospora, Bacillus, Cellulomonas* and *Streptomyces*. The enzymes secreted by these microorganisms have three types of activities which are of use in the conversion of cellulose to glucose and are divided up into three groups: endoglucanases, which randomly attack cellulose fibers internally, exoglucanases which will attack the ends of the fibers, releasing cellobiose, and beta-glucosidases which will hydrolyze this cellobiose to glucose. The latter constitute the limiting step of the cellulose conversion process. Indeed, the first difficulty of the process lies in the conversion of the cellobiose to glucose, since any cellobiose not hydrolyzed at the end of the process represents a loss of yield during the production of biofuel.

This accumulation of cellobiose is a major problem in enzymatic hydrolysis, given that several cellulase-producing microorganisms, including *Trichoderma*, produce very little beta-glucosidase. In fact, less than 1% of the total proteins secreted by industrial *Trichoderma* strains are of beta-glucosidase type. This low amount of beta-glucosidase therefore results in a low capacity to hydrolyze cellobiose to glucose, hence its accumulation in the system. As it happens, a high concentration of cellobiose inhibits the activity of the other cellulases and in particular the exoglucanases for which cellobiose is the final product of the reaction. In order to overcome these drawbacks, the inventors have developed, in their patent application WO 2010/029259, beta-glucosidase genes which make it possible to obtain enzymes with increased specific activity, thereby substantially improving the process for converting lignocellulosic biomass to biofuel.

The hydrolysis and the fermentation can be carried out according to various schemes. The most common consists of separate hydrolysis and fermentation (SHF). This method makes it possible to optimize each step by maintaining the optimum reaction conditions. This fermentation is carried out extemporaneously, at a temperature of between about 28° C. and about 30° C. while the hydrolysis is generally carried out at a temperature of at least 45° C. However, in SHF, the sugars released at the end of the reaction are at a very high concentration and lead to an inhibition of the enzymes, slowing down the efficiency of the process.

In order to avoid these drawbacks, another type of process (SSF—Simultaneous Saccharification and Fermentation) can be envisioned. In SSF, the two steps (hydrolysis and fermentation of hexoses) take place simultaneously, preventing the accumulation of sugars at concentrations which are inhibitory for the enzymes. The investment costs are also reduced subsequent to the use of a single reactor. The degree of hydrolysis is higher subsequent to the absence of inhibition since the sugars released are used immediately for the fermentation to ethanol.

In this method, the temperature of the reactor necessarily constitutes a compromise between the optimum temperatures for hydrolysis and for fermentation, typically between about 30° C. and about 35° C. However, at such a temperature, the activity of the cellulolytic enzymes, including beta-glucosidase, is reduced by about 30%.

There is therefore a need for enzymes capable of maintaining an efficient beta-glucosidase activity at the optimum hydrolysis and fermentation temperatures of an SSF process, in particular at a temperature of between about 30° C. and about 35° C.

The inventors have developed a polypeptide which has enhanced beta-glucosidase activity at a temperature of between about 30° C. and about 35° C., in particular compared with the beta-glucosidase activity of the wild-type BGL1 protein of sequence SEQ ID No. 3. BGL1 corresponds to the beta-glucosidase from *Trichoderma reesei*.

The inventors have previously identified several clones which have enhanced specific beta-glucosidase activity compared with the beta-glucosidase activity of the wild-type BGL1 protein. Such results are presented in their patent application WO 2010/029259. More specifically, they have demonstrated a particular clone encoding a polypeptide of SEQ ID No. 5 (called 100B11), the expression of which in *Trichoderma reesei* under the control of a strong promoter leads to a 26.2-fold increase in the beta-glucosidase activity (table 6 of patent application WO 2010/029259) of the enzymatic cocktail produced compared with that produced by a strain not expressing this enzyme.

They have now demonstrated, surprisingly and unexpectedly, a new clone, which encodes an enzyme which has enhanced activity compared with the previously identified clone 100B11, this being at a temperature of between about 30° C. and about 35° C.

The invention therefore relates to a polypeptide which has beta-glucosidase activity, of amino acid sequence SEQ ID No. 1.

The amino acid sequence of the polypeptide of the invention is as follows:

MRYRTAAALALATGPFARADSHSTSGASAEAVVPPAGTPWGTAYDKAKA

ALAKLNLQDKVGIVSGVGWNGGPCVGNTSPASKIGYPQLCLQDGPLGIR

FGGSVTAFTPGIQAASTWDTELMRQRGEYLGAEAKGCGIHVLLGPVAGP

LGKTPQGGRNWEGFGVDPYLTGIAMAETIEGLQSAGVQACAKHYIVNEQ

```
-continued
ELNRETISSNPDDRTLHELYLWPFADAVHANVASVMCSYNKINGSWACE

DQYTLQTVLKDQLGFPGYVMTDWNAQHTTVQSANSGLDMSMPGTDFNGN

NRLWGPALTNAVNSNQVPTSRVDDMVTRILAAWYLTGQDQAGYPSFNIS

RNVQGNHKTNVRAIARDGIVLLKNDANILPLKKPASIAVVGSAAIIGNH

ARNSPSCNDKGCDDGALGMGWGSGAVNYPYFVAPYDAINTRASSQGTQV

TLSNTDNTSSGASAARGKDVAIVFITADSGEGYITVEGNAGDRNNLDPW

HNGNALVQAVAGANSNVIVVVHSVGAIILEQILALPQVKAVVWAGLPSQ

ESGNALVDVLWGDVSPSGKLVYTIAKSPNDYNTRIVSGGSDSFSEGLFI

DYKHFDDANITPRYEFGYGLSYTKFNYSRLSVLSTAKSGPATGAVVPGG

PSDLFQNVATVTVDIANSGQVTGAEVAQLYITYPSSAPRTPPKQLRGFA

KLNLTPGQSGTATFNIRRRDLSYWDTASQKWVVPSGSFGISVGASSRDI

RLTSTLSVA.
```

This polypeptide is encoded by the nucleic acid sequence SEQ ID No. 2.

Preferentially, said polypeptide of amino acid sequence SEQ ID No. 1 has enhanced beta-glucosidase activity at a temperature of between about 30° C. and about 35° C., in particular compared with the beta-glucosidase activity of the wild-type BGL1 protein of sequence SEQ ID No. 3 at these same temperatures. The BGL1 protein is encoded by the nucleic acid sequence SEQ ID No. 4.

More preferentially, said polypeptide of amino acid sequence SEQ ID No. 1 has enhanced beta-glucosidase activity at a temperature of between about 30° C. and about 35° C. compared with the beta-glucosidase activity of the 100B11 polypeptide of amino acid sequence SEQ ID No. 5 at these same temperatures. The 100B11 polypeptide is encoded by the nucleic acid sequence SEQ ID No. 6.

Furthermore, the polypeptide according to the invention has the advantage of being less sensitive to inhibition by glucose and as a result retains a better beta-glucosidase activity in the presence of a high glucose concentration.

In one embodiment, the polypeptide as previously described has a beta-glucosidase activity determined in the presence of glucose which is enhanced compared with the beta-glucosidase activity of the wild-type protein BGL1 (SEQ ID No. 3) determined in the absence of glucose.

In one preferred embodiment, the polypeptide of the invention has a beta-glucosidase activity which is enhanced by at least 10%, preferentially by at least 20%, preferentially by at least 30%, even more preferentially by at least 40% at a temperature of between about 30° C. and about 35° C. compared with the beta-glucosidase activity of the 100B11 polypeptide of amino acid sequence SEQ ID No. 5.

Those skilled in the art will, for example, be able to determine the increase or in other words the improvement of the enzymatic activity of a polypeptide according to the invention by means of an enzymatic activity test using the substrate para-nitrophenyl beta-D-glucopyranoside (pNPG). The amount of para-nitrophenol obtained after action of the beta-glucosidase may, for example, be determined by reading the optical density at 414 nm.

An example of a protocol, which those skilled in the art may use to determine whether a polypeptide according to the invention has enhanced enzymatic activity compared with that of the wild-type BGL1 protein, is the following:
  preparation of a stock culture of *E. coli* expressing a polypeptide according to the invention, overnight at 37° C.;
  inoculation of an LB culture medium with 1% of stock culture for 24 h at 20° C.;
  centrifugation for 2 minutes at 13 000 rpm;
  resuspension of the cell pellets with 100 mM succinate buffer at pH 5 (final $OD_{600}$=100);
  incubation of 50 µl of cells with 100 µl of 100 mM succinate buffer at pH 5 containing 15 mM of para-nitrophenyl beta-D-glucopyranoside (pNPG) for 1 h30 at 50° C., followed by 5 minutes on ice;
  addition of 150 µl of 0.2 M $Na_2CO_3$;
  centrifugation for 2 minutes at 13 000 rpm;
  reading of the optical density at 414 nm on 150 µl of supernatant.

Furthermore, those skilled in the art will be able to use the protocol described above by incubating the 50 µl of cells with 100 µl of 100 mM succinate buffer at pH 5 containing 15 mM of pNPG and 60 g/l of glucose for 1 h30 at 50° C., in order to determine whether a polypeptide according to the invention is less sensitive to glucose inhibition than the wild-type BGL1 protein.

These protocols are easily adaptable for measuring the enhancement of the beta-glucosidase activity under temperature conditions of between about 30° C. and about 35° C., in particular compared with the 100B11 polypeptide of amino acid sequence SEQ ID No. 5.

The invention also relates to a nucleic acid encoding the polypeptide of amino acid sequence SEQ ID No. 1. Preferentially, said nucleic acid comprises the nucleic acid sequence SEQ ID No. 2.

The invention also relates to a vector comprising a nucleic acid as previously described.

According to the invention, the term "vector" is intended to mean any DNA sequence into which it is possible to insert foreign nucleic acid fragments, the vectors making it possible to introduce foreign DNA into a host cell. Examples of vectors are plasmids, cosmids, yeast artificial chromosomes (YACs), bacterial artificial chromosomes (BACs) and P1 bacteriophage-derived artificial chromosomes (PACs), and virus-derived vectors.

According to the invention, the nucleic acid as previously described may be functionally linked to a promoter, a terminator or any other sequence required for its expression in the host cell.

The vector according to the invention may also carry a selectable marker. The term "selectable marker" is intended to mean a gene of which the expression confers on the cells that contain it a characteristic which makes it possible to select them. It is, for example, a gene for resistance to antibiotics.

A subject of the invention is also an isolated host cell capable of producing the polypeptide of the invention as previously described, or comprising a nucleic acid encoding said polypeptide of the invention.

Those skilled in the art will be able to introduce at least the polypeptide, the nucleic acid or the vector as previously described into the host cell by means of well-known conventional methods. For example, mention may be made of calcium chloride treatment, electroporation, or the use of a particle gun.

According to one embodiment, those skilled in the art will be able to introduce into the host cell, and by conventional methods, several copies of a nucleic acid encoding a polypeptide which has enhanced beta-glucosidase activity according to the invention.

According to one embodiment, the isolated host cell as previously described is chosen from *Trichoderma, Aspergillus, Neurospora, Humicola, Myceliophthora, Chrysospo-*

*rium, Penicillium, Fusarium, Thermomonospora, Bacillus, Pseudomonas, Escherichia, Clostridium, Cellulomonas, Streptomyces, Yarrowia, Pichia* and *Saccharomyces*.

According to one preferred embodiment, the isolated host cell as previously described is chosen from *Trichoderma reesei, Trichoderma viridae, Trichoderma koningii, Aspergillus niger, Aspergillus nidulans, Myceliophthora thermopila, Chrysosporium lucknowense, Aspergillus wentii, Aspergillus oryzae, Aspergillus phoenicis, Neurospora crassa, Humicola grisae, Penicillium pinophilum, Penicillium oxalicum, Escherichia coli, Clostridium acetobutylicum, Clostridium saccharolyticum, Clostridium benjerinckii, Clostridium butylicum, Pichia pastoris, Yarrowia lipolityca, Saccharomyces cerevisiae*, and mixtures thereof.

According to one preferred embodiment, the isolated host cell as previously described is chosen from *Trichoderma reesei* and *Saccharomyces cerevisiae*.

The invention also relates to the use of the polypeptide as previously described or any one of the cells as previously described, for the hydrolysis of beta-oligosaccharides.

The invention also relates to the use of the polypeptide as previously described or any one of the cells previously described, for the hydrolysis of cellobiose to glucose.

A subject of the invention is also the use of the polypeptide as previously described or any one of the cells previously described, for the production of biofuel.

According to the invention, the term "biofuel" can be defined as any product which results from the conversion of the biomass and which can be used for energy purposes. Firstly, and without wishing to be limited, mention may be made, by way of example, of biogases, products which can be incorporated (optionally after subsequent conversion) into a fuel or can be a fuel in its own right, such as alcohols (ethanol, butanol and/or isopropanol depending on the type of fermentative organism used), solvents (acetone), acids (butyric acid), lipids and derivatives thereof (short- or long-chain fatty acids, fatty acid esters), and also hydrogen.

Preferably, the biofuel according to the invention is an alcohol, for example ethanol, butanol and/or isopropanol. More preferentially, the biofuel according to the invention is ethanol.

In another embodiment, the biofuel is biogas.

In another embodiment, the product is a molecule which is advantageous in the chemical industry, for instance other alcohols, such as 1,2-propanediol, 1,3-propanediol, 1,4-butanediol, 2,3-butanediol, organic acids such as acetic acid, propionic acid, acrylic acid, butyric acid, succinic acid, malic acid, fumaric acid, citric acid or itaconic acid, or hydroxy acids such as glycolic acid, hydroxypropionic acid or lactic acid.

In addition to the production of biofuel, the polypeptide which has enhanced beta-glucosidase activity at a temperature of between 30° C. and 35° C. may also be used in other types of applications by catalyzing the hydrolysis of various substrates, thus enabling the release of a variety of aromas/flavors. By way of example, it may be used in order to release fruit flavors by hydrolyzing several glucosides present within these fruits, or else it may hydrolyze grape monoterphenyl beta-glucosides, thus representing an important source of flavors for wine. Consequently, the polypeptide as previously described may be used in several fields, in particular in perfumery, in the food industry, in enology, etc.

The strains of filamentous fungi, preferably *Trichoderma*, more preferentially *T. reesei*, capable of expressing the polypeptide according to the invention are cultured in fermenters, in the presence of a carbon-based substrate, such as lactose or glucose, chosen for the growth of the microorganism. In one embodiment, this carbon-based substrate, depending on its nature, is introduced into the fermenter before sterilization or is sterilized separately and introduced into the fermenter after sterilization of the latter so as to obtain an initial concentration of 20 to 35 g/l.

An aqueous solution containing the substrate chosen for the production of the enzymes is then added. An enzymatic composition which acts on lignocellulosic biomass, produced by the fungi, is finally recovered by filtration of the culture medium. This composition contains in particular endoglucanases, exoglucanases and the beta-glucosidase according to the invention. In one embodiment, the aqueous solution containing the substrate chosen from the production of the enzymes is prepared at the concentration of 200-250 g/l; this solution must contain an inducer substrate such as lactose. This aqueous solution is injected after the exhaustion of the initial carbon-based substrate so as to provide an optimized amount, of between 35 and 45 mg/g, of cells (fed batch). During this fed batch phase, the residual concentration of sugar in the culture medium is less than 1 g/l and the enzymes which act on lignocellulosic biomass are secreted by the fungus. Said enzymes can be recovered by filtration of the culture medium.

A subject of the invention is an enzymatic composition which acts on lignocellulosic biomass, said enzymatic composition being produced by filamentous fungi or yeasts and comprising the polypeptide as previously described.

Finally, a subject of the invention is a process for producing biofuel from biomass, comprising the following steps:
  suspension, in an aqueous phase, of the material to be hydrolyzed;
  hydrolysis, in the presence of an enzymatic composition, of the lignocellulosic biomass as previously described so as to produce a hydrolysate containing glucose;
  fermentation of the glucose of the hydrolysate;
  separation of the biofuel from the fermentation must,
characterized in that the hydrolysis and fermentation steps are carried out simultaneously.

Another subject of the invention is a process for producing biofuel from biomass, characterized in that it comprises the following steps:
  suspension, in an aqueous phase, of the biomass to be hydrolyzed;
  simultaneous addition of an enzymatic composition which acts on the lignocellulosic biomass as previously defined and of a fermentative organism and incubation;
  separation of the biofuel from the fermentation must.

Another subject of the invention is a process for producing biofuel from biomass, characterized in that it comprises the following successive steps:
  suspension, in an aqueous phase, of the biomass to be hydrolyzed;
  addition of one or more cellulolytic and/or fermentative organisms as previously defined at a temperature of between 30° C. and 35° C. so as to produce a fermentation must;
  separation of the biofuel from the fermentation must.

According to this embodiment, the cellulose present in the biomass is converted to glucose, and at the same time, in the same reactor, the fermentative organism (for example a yeast) converts the glucose to final product according to an SSF (Simultaneous Saccharification and Fermentation) process known to those skilled in the art. Depending on the metabolic and hydrolytic capacities of the fermentative organism, the correct performing of the operation may require the addition of a greater or lesser amount of exogenous cellulolytic mixture.

In another embodiment, the fermentative organism produces the polypeptide which is the subject of the invention by secretion or on the surface of its cell, optionally together with other enzymes which act on lignocellulosic biomass, thus limiting or eliminating the need for enzymes produced by the filamentous fungus.

The use of the polypeptide which exhibits better beta-glucosidase activity at a temperature of between about 30° C. and about 35° C. according to the present invention thus has the advantage of obtaining a better glucose production yield. Thus, the present invention makes it possible to use less enzyme than previously, which has an economic advantage, the biofuel production cost, for example, being less.

Other aspects, subjects, advantages and characteristics of the invention will be presented on reading the nonrestrictive description which follows and which describes preferred embodiments of the invention, given by means of examples.

EXAMPLES

Example 1

1$^{st}$ Round of Shuffling

The sequence of the *Trichoderma reesei* beta-glucosidase gene (parental gene BGL1, SEQ ID No. 4) was subjected to a first round of shuffling according to the patented process described in EP 1 104 457 B1 with the putative glucosidase gene of *Chaetomium globosum* (gene A) (SEQ ID No. 7, encoded by the nucleic acid sequence SEQ ID No. 8) having 70% identity with the BGL1 parental gene.

1—High-Throughput Screening

A high-throughput screening test made it possible to select the best clones resulting from the shuffling of these two sequences, i.e. those having an enhancement factor greater than 2 at the beta-glucosidase activity level when compared with the BGL1 parental gene from *T. reesei*.

The library screening test of the first round of shuffling was carried out according to the following steps:
  isolation on agar of the various colonies of *E. coli* expressing the shuffling variants of the recombinant enzyme according to the invention and preculture of said colonies in LB medium overnight at 37° C.;
  inoculation of an LB medium at 3% with the preculture, then incubation for 4 h at 37° C.;
  induction of the expression of the variants by addition of 100 μM isopropyl-beta-thio-galactoside (IPTG), then incubation at 20° C. overnight;
  centrifugation for 2 minutes at 13 000 rpm;
  resuspension of the cell pellets in 100 μl of 0.1 M succinate buffer containing 2.2 mM of para-nitrophenyl beta-D-glucopyranoside (pNPG);
  incubation for 3 h at ambient temperature;
  reading of the optical density at 414 nm after alkalinization.

Under these screening conditions, several clones exhibiting an enhancement of the beta-glucosidase activity compared with the BGL1 reference enzyme were identified.

2-Determination of the Enhancement of the Beta-Glucosidase Activity 2-1/On the pNPG Substrate In order to determine the relative kcat of the variants selected in the first round of shuffling, the following procedure was carried out:
  formation of a stock culture of *E. coli* expressing a recombinant enzyme according to the invention, overnight at 37° C.;
  inoculation of an LB culture medium with 1% stock culture for 24 h at 20° C. with IPTG (250 μM) induction;
  centrifugation for 2 minutes at 13 000 rpm;
  resuspension of the cell pellets with 100 mM succinate buffer at pH 5 (final $OD_{600}$=100);
  incubation of 50 μl of cells with 100 μl of 100 mM succinate buffer at pH 5 containing 15 mM of para-nitrophenyl beta-D-glucopyranoside (pNPG) for 1 h30 at 50° C., followed by 5 minutes on ice;
  addition of 150 μl of 0.2 M $Na_2CO_3$;
  centrifugation for 2 minutes at 13 000 rpm;
  reading of the optical density at 414 nm on 150 μl of supernatant.

Table 2 gives the kcat values and also the enhancement factors obtained for three previously identified clones (called 10H7, 59B8 and 164A2) under these experimental conditions.

TABLE 2

Enhancement of the beta-glucosidase activity
(results of the induced cultures)

| | Clones | $K_{cat}$ (min$^{-1}$) | Enhancement factor |
|---|---|---|---|
| 1$^{st}$-round clones | 10H7 | 590.0 | 8 |
| | 59B8 | 518.6 | 7 |
| | 164A2 | 1437.3 | 20 |
| Reference protein | BGL1 | 71.0 | 1 |

The results show very significant enhancements of enzymatic activities compared with the wild-type enzyme (BGL1) for the 3 clones 10H7, 59B8 and 164A2.

2-2/On Cellobiose

The enhancement of activity of the 10H7, 59B8 and 164A2 clones was then confirmed on a second substrate: cellobiose.

This test was carried out on cultures of *E. coli* expressing a recombinant enzyme according to the invention. The steps of the test are the following:
  inoculating an LB culture medium with 1% of stock culture induced with IPTG, then incubation overnight at 37° C.;
  culturing said cells at 37° C. until an optical density at 600 nm of 0.4 is obtained;
  inducing said cells with 250 μM IPTG at 20° C. for 20 hours;
  washing the cell pellets three times in a 100 mM succinate buffer, pH 5, in order to remove the culture medium glucose;
  preparing a reaction mix (RM1) consisting of 10 μl of said cells and of 190 μl of cellobiose at 263.2 mM (final concentration 250 mM) for 12 hours at 50° C. in a microplate;
  incubating for 12 hours at 50° C. in a microplate.

Revelation:
Prepare a reaction mix (RM2) consisting of:
  10 μl of RM1,
  90 μl of 100 mM succinate buffer at pH 5,
  5 μl of glucose oxidase at 44 U/ml.
Incubate for 1 h at ambient temperature.
Mix and incubate the following for 30 min at ambient temperature:
  10 μl of RM2,
  2 μl of horseradish peroxidase at 10 U/ml,
  5 μl of 100 mM ABTS,
  83 μl of 50 mM phosphate buffer, pH 7.4.
Read the optical densities at 420 nm.

TABLE 3

Enhancement of the beta-glucosidase activity
(results of the induced cultures)

|  | Clones | $K_{cat}$ (min$^{-1}$) | Enhancement factor |
|---|---|---|---|
| 1$^{st}$-round clones | 10H7 | 69.1 | 13 |
|  | 59B8 | 37.7 | 7 |
|  | 164A2 | 213.2 | 41 |
| Reference protein | BGL1 | 5.2 | 1 |

Likewise, the results show very significant enhancements of enzymatic activities compared with the wild-type enzyme (BGL1) for the 10H7, 59B8 and 164A2 clones when cellobiose is used as substrate.

Example 2

2$^{nd}$ Round of Shuffling

The sequences of the enhanced genes obtained in the first round of shuffling was subsequently subjected to a second round of shuffling (still according to the patented process described in EP 1 104 457 B1). In order to increase the genetic diversity, at least one gene encoding a beta-glucosidase having 70% identity with the wild-type BGL1 enzyme was added.

More specifically, the putative glucosidase gene of *Neurospora crassa* (gene C) (SEQ ID No. 9 encoded by the nucleic acid sequence SEQ ID No. 10) was used.

1—High-Throughput Screening

A high-throughput screening test as previously described (with the exception of the IPTG induction step, since the enhancement provided in the first round of shuffling allows detection of the beta-glucosidase activity based only on promoter leakage) was carried out on the clones obtained following this second round of shuffling, in order to select the best clones, i.e. those which exhibit an enhancement factor greater than 2 at the beta-glucosidase activity level when compared with the 164A2 clone.

Under these screening conditions, an enhancement of the beta-glucosidase activity compared with the reference enzyme (164A2) was found in several clones, including in particular the 100B11 (SEQ ID No. 5 encoded by the nucleic acid sequence SEQ ID No. 6) and 115E1 (SEQ ID No. 11 encoded by the nucleic acid sequence SEQ ID No. 12) clones.

2-Determination of the Enhancement of the Beta-Glucosidase Activity 2-1/On pNPG

In order to determine the relative kcat, the activities of the 100B11 and 115E1 clones were measured by means of the activity test as previously described.

Table 4 gives the kcat values and also the enhancement factors obtained for the 100B11 and 115E1 clones under these experimental conditions.

TABLE 4

Enhancement of the beta-glucosidase activity
(results of the induced cultures)

|  | Clones | $K_{cat}$ (min$^{-1}$) | Enhancement factor |
|---|---|---|---|
| 2$^{nd}$-round clones | 100B11 | 4342.8 | 3.0 |
|  | 115E1 | 3989.2 | 2.8 |
| Reference protein | 164A2 | 1437.3 | 1 |

The results show very significant enhancements of enzymatic activities compared with the reference enzyme (164A2) and with BGL1 (X60) for the 100B11 and 115E1 clones.

2-2/On Cellobiose

The enhancement of activity of the 100B11 and 115E1 clones was then confirmed on a second substrate: cellobiose.

In order to determine the relative kcat, the activities of the 100B11 and 115E1 clones were measured by means of the activity test at 50° C. as previously described using cellobiose as substrate as described in point 2-2 of example 1.

TABLE 5

Enhancement of the beta-glucosidase activity
(results of the induced cultures)

|  | Clones | $K_{cat}$ (min$^{-1}$) | Enhancement factor |
|---|---|---|---|
| 2$^{nd}$-round clones | 100B11 | 387.2 | 1.8 |
|  | 115E1 | 406.4 | 1.9 |
| Reference protein | 164A2 | 213.2 | 1 |

Likewise, the results show significant enhancements of enzymatic activities compared with the reference enzyme (164A2) for the 100B11 and 115E1 clones when cellobiose is used as substrate.

Example 3

3$^{rd}$ Round of Shuffling

The sequences of 14 enhanced genes (138E12, 134G2, 100B11, 115E1, 99G11, 127B12, 91F6, 135F9, 116D9, 212D11, 210A6, 124F5, 129D2 and 141F7) obtained in the second round of shuffling were subsequently subjected to a third round of shuffling (still according to the patented process described in EP 1 104 457 B1). In order to increase the genetic diversity, at least one gene encoding a beta-glucosidase having 70% identity with these genes was added. In this precise example, the putative beta-glucosidase gene of *Neurospora crassa* (gene C) (SEQ ID No. 9 encoded by the nucleic acid sequence SEQ ID No. 10) and the putative beta-glucosidase gene of *Chaetomium globosum* (gene A) (SEQ ID No. 7 encoded by the nucleic acid sequence SEQ ID No. 8) were used.

1—High-Throughput Screening

A high-throughput screening test as previously described (with the exception of the IPTG induction step, since the enhancement provided in the first round of shuffling allows detection of the beta-glucosidase activity based only on promoter leakage) was carried out on the clones obtained following this third round of shuffling. The activity of these clones was measured at 30° C. and at 50° C.

Under these screening conditions, the 17E5 clone (of amino acid sequence SEQ ID No. 1, encoded by the nucleic acid sequence SEQ ID No. 2) was selected since it has an advantageous 30° C./50° C. activity ratio.

Table 6 gives the relative activities obtained at 50° C. and at 30° C. for the 17E5 clone and for the 100B11 clone (reference clone resulting from the second round of shuffling).

TABLE 6

Relative activities at 30° C.

|       | 50° C. | 30° C. |
|-------|--------|--------|
| 17E5  | 100%   | 80%    |
| 100B11| 100%   | 53%    |

The results show that the 17E5 clone retains 80% activity at 30° C. compared with its activity at 50° C., versus 53% for the 100B11 clone.

Furthermore, its specific activity is greater by a factor of 2 than that of the 100B11 enzyme.

2—Determination of the Beta-Glucosidase Activity

In order to determine the relative kcat, the activity of the 17E5 clone was measured at 30° C. and at 50° C. by means of the activity test as previously described.

Table 7 gives the kcat value and also the enhancement factor obtained for the 17E5 clone under these experimental conditions.

TABLE 7

Enhancement of the beta-glucosidase activity at 30° C. (results of the noninduced cultures)

|        | kcat (min$^{-1}$) | | enhancement | |
|--------|--------|--------|--------|--------|
|        | 30° C. | 50° C. | 30° C. | 50° C. |
| 17E5   | 4.2    | 10.94  | 2.32   | 2.17   |
| 100B11 | 1.81   | 5.03   |        |        |

The results show an enhancement of the enzymatic activity of the 17E5 clone by a factor of 2 compared with the reference clone, this being at both temperatures.

Example 4

Expression of the Enhanced Variants of Beta-Glucosidases in *Trichoderma reesei*

The 17E5 gene was cloned into a vector allowing expression in a *Trichoderma reesei* strain derived from RUT C30 (ATCC 56765), CL847 (Durand et al., Enzyme Microb. Technol., 1988; 10:341-346) with selection using hygromycin (*Streptomyces hygroscopicus* Hph gene). The 17E5 gene was placed under the control of a cbh1 strong promoter inducible at the same time as the other *T. reesei* cellulases.

The transformation of *Trichoderma reesei* was carried out according to the conventional methods known to those skilled in the art (transformation of protoplasts by calcium shock and selection with 50 µg/ml hygromycin). The transformants were purified by sporulation and then subcultured twice in selective medium in order to eliminate the unstable clones.

Thirty clones were then evaluated with respect to cellulase production in 24-well plates. A few spores of each clone were used to inoculate 2 ml of a medium having the following composition: 20 g/l lactose, 20 g/l Solka floc cellulose, 5 g/l peptone, 15 g/l KH$_2$PO$_4$, 5 g/l (NH$_4$)$_2$SO$_4$, 0.6 g/l CaCl$_2$, 0.6 g MgSO$_4$, 0.005 g/l FeSO$_4$, 0.0014 g/l MnSO$_4$, 0.0014 g/l ZnSO$_4$, 0.0037 g/l CoCl$_2$, 11.6 g/l of maleic acid, 12.1 g/l of tris and 2.08 g/l of NaOH. The flasks were incubated at 30° C. with shaking at 150 rpm.

After 5 days, the cultures were centrifuged and the protein concentration of the supernatant was measured using the Folin method. The beta-glucosidase activity of the supernatants was measured by hydrolysis of the para-nitrophenyl beta-D-glucopyranoside (pNPG) chromophore substrate under the following conditions:

50 mM of citrate buffer at pH 4.8
5 mM of pNPG
10 µl of sample
incubation at 30° C. for 30 min.

The reaction was stopped by adding 100 µl of 2% sodium carbonate. The amount of para-nitrophenol released by hydrolysis of the pNPG was measured by measuring the absorbance at 410 nm and compared with a para-nitrophenol range. The reaction was linear from 25 to 400 µM of para-nitrophenol. The samples were optionally diluted so that the absorbance measured remains in the linearity of the range. The beta-glucosidase activity was also measured at 50° C., under the same conditions as above, for comparison. The clones exhibiting the highest beta-glucosidase activity (greater at least by a factor of 5 compared with the strain of origin) were selected.

Table 8 shows the 30° C./50° C. pNPase beta-glucosidase activities measured in µmol/min/mg of enzyme for supernatants derived, respectively, from a wild-type CL847 strain, from a strain expressing the variant 100B11 and from one of the clones expressing the variant 17E5, obtained according to the method described above.

TABLE 8

Beta-glucosidase activities of wild-type CL847, of the 100B11 polypeptide and of the 17E5 polypeptide

|        | 30° C./50° C. activity ratio | Specific activity at 30° C. | Specific activity at 50° C. |
|--------|------|------|------|
| CL847  | 0.2  | 0.06 | 0.3  |
| 100B11 | 0.3  | 3.7  | 12.5 |
| 17E5   | 0.5  | 4.7  | 9.5  |

An increase in the 30° C./50° C. ratio is noted in the 17E5 clone, with a specific activity greater than that of the 100B11 variant at the temperature of 30° C.

Example 5

Recombinant Expression of the Wild-Type Beta-Glucosidase (BGL1) and of the Enhanced Variants 100B11 and 17E5 in *Saccharomyces Cerevisiae*

1—Production of the BGL1, 100B11 and 17E5 Proteins in Yeast Cytoplasm:

The wild-type beta-glucosidase gene of *Trichoderma reesei* (BGL1) and also those of the 100B11 and 17E5 variants were cloned without signal peptide into the pESC-Leu vector (Agilent Technologies). This construct allows the expression of the protein in the cytoplasm of the *Saccharomyces cerevisiae* EBY100 strain, which is auxotrophic with respect to leucine and tryptophan (Boder E T and Wittrup K D, Biotechnol Prog, 1998, 14:55-62). This plasmid makes it possible to place the gene expression under the control of the galactose-inducible GAL1 promoter, and possesses the selectable auxotrophic marker gene (Leu2) which allows the selection of the transformants. The protein produced is finally fused to the N-terminal c-myc tag, allowing the detection and the purification of the enzyme produced by affinity chromatography.

The transformation of *S. cerevisiae* EBY100 was carried out according to the conventional methods known to those skilled in the art (transformation of yeasts by heat shock and lithium acetate). The transformants were selected on YNB-Glc-Trp medium containing 0.67% of Yeast Nitrogen Base (YNB), 2% of glucose and 0.01% of tryptophan.

One transformant for each gene (Sc-BGL1, Sc-100B11 and Sc-17E5) was used to inoculate 15 ml of a YNB-Glc-CAA-Trp minimum medium containing 0.67% of YNB, 0.5% of casamino acid (CAA), 0.01% of tryptophan and 2% of glucose. After 24 h of preculture at 30° C. with shaking at 220 rpm, the three Sc-BGL1, Sc-100B11 and Sc-17E5 strains were used to inoculate (at an $OD_{600}$ of 0.5) 150 ml of YNB-Gal-CAA-Trp medium containing 0.67% of YNB, 0.5% of CAA, 0.01% of tryptophan and 2% of galactose. The cultures were incubated at 25° C. with shaking at 220 rpm.

After 4 days of incubation, 20 ml of culture were centrifuged at 3000 g, at 4° C. for 5 min. The yeast pellets were taken up in 3 ml of 50 mM citrate buffer, pH 5, and mechanically lysed with a pressure of 2.5 kbar. The cytoplasmic extract was obtained after centrifugation for 30 min at 50 000 g at 4° C.

2—Determination of the Beta-Glucosidase Activity

The total protein concentration in the cytoplasmic extract was estimated on average, by Bradford assay (Bradford M M., Anal Biochem, 1976, 72:248-54), at 1.7 mg/ml.

The beta-glucosidase activity of the cytoplasmic extracts was measured by hydrolysis of the para-nitrophenyl beta-D-glucopyranoside (pNPG) substrate in a volume of 600 μl under the following conditions:

50 mM of citrate buffer at pH 5
5 mM of pNPG
3.6 μl of cytoplasmic extract containing 6.1 μg of total proteins
Incubation at 30° C. or 50° C. for 30 min.

The reaction was stopped by adding 100 μl of 1M sodium carbonate to 100 μl of hydrolysis reaction. The concentration of para-nitrophenol (pNP) released by hydrolysis of the pNPG was determined by measuring the absorbance at 415 nm and compared with a standard range of para-nitrophenol (linear from 0.36 μM to 360 μM). The cytoplasmic extracts were optionally diluted in order to be under initial reaction rate conditions.

Table 9 shows the 30° C./50° C. beta-glucosidase activity ratios measured in $\mu mol \cdot min^{-1} \cdot mg^{-1}$ of total proteins for cytoplasmic extracts derived, respectively, from a strain expressing the wild-type enzyme (Sc-BGL1), from a strain expressing 100B11 (Sc-100B11) and from a strain expressing 17E5 (Sc-17E5).

TABLE 9

Beta-glucosidase activities of Sc-BGL1, Sc-100B11 and Sc-17E5

|  | Specific activity at 30° C. | Specific activity at 50° C. | 30° C./ 50° C. activity ratio | Enhancement of the specific activity at 30° C. compared with wild-type BGL1 |
|---|---|---|---|---|
| Sc-BGL1 | 0.15 | 0.41 | 0.4 | — |
| Sc-100B11 | 0.18 | 0.64 | 0.3 | 1.2 |
| Sc-17E5 | 0.46 | 1.12 | 0.4 | 3.1 |

The results show that the specific activity at 30° C. of the Sc-17E5 strain is greater by a factor of 3 compared with the Sc-BGL1 strain and by a factor of 2.5 compared with Sc-100B11.

Example 6

Purification and Characterization of the Wild-Type Beta-Glucosidase (BGL1) and of the Enhanced Variants 100B11 and 17E5 Produced in *S. Cerevisiae*

1—Beta-Glucosidase Purification:

The cytoplasmic extracts of Sc-BGL1 and of the Sc-100B11 and Sc-17E5 variants of example 5 were used to purify the corresponding enzymes, BGL1, 100B11 and 17E5, according to the following protocol:

500 μl of cytoplasmic extract were incubated with 20 μl of "Anti-c-Myc tag Gel" resin (MBL) for 1 h at 4° C. with axial shaking. After 10 seconds of centrifugation at 13 000 rpm, the resin was washed 3 times with 1×PBS. After incubation of the resin for 5 min at 4° C. in an elution solution composed of the c-myc peptide (EQKLISEEDL) at 1 $mg \cdot ml^{-1}$, the elution of the protein was carried out by centrifugation for 10 seconds at 13 000 rpm.

2—Determination of the Beta-Glucosidase Activity

The concentration of the purified enzymes was obtained by measuring the absorbance at 280 nm with a nanodrop, using a molar extinction coefficient equal to 120 125 $M^{-1} \cdot cm^{-1}$ for native BGL1 and 120 250 $M^{-1} \cdot cm^{-1}$ for 100B11 and 17E5. Said concentration is on average equal to 0.19 mg/ml.

The purity of each enzyme was verified by electrophoresis on a 10% polyacrylamide gel in the presence of SDS with protein staining using Coomassie blue.

The activity of BGL1 and of the purified 100B11 and 17E5 variants was measured at 30° C. and at 50° C. as previously described.

Table 10 shows the specific activities of each enzyme (in $\mu mol \cdot min^{-1} \cdot mg^{-1}$ of enzyme) determined during the hydrolysis of pNPG at 30° C. and 50° C.

TABLE 10

Beta-glucosidase activities of purified BGL1, 100B11 and 17E5

|  | Specific activity at 30° C. | Specific activity at 50° C. | 30° C./ 50° C. activity ratio | Enhancement of the specific activity at 30° C. compared with wild-type BGL1 |
|---|---|---|---|---|
| BGL1 | 5.1 | 8.9 | 0.57 | — |
| 100B11 | 7.1 | 17.2 | 0.41 | 1.4 |
| 17E5 | 10.2 | 23.6 | 0.43 | 2.0 |

The results show an enhancement at 30° C. of the specific activity of the 17E5 variant by a factor of 2 compared with wild-type BGL1 and of 1.4 compared with the 100B11 variant.

The invention claimed is:

1. A variant polypeptide having beta-glucosidase activity and comprising the amino acid sequence of SEQ ID NO: 1.

2. The variant polypeptide of claim 1, wherein the variant polypeptide has enhanced beta-glucosidase activity at a temperature between 30° C. and 35° C. compared with the beta-glucosidase activity of a wild-type BGL1 protein comprising the amino acid sequence of SEQ ID NO: 3.

3. The variant polypeptide of claim 1, wherein the variant polypeptide has enhanced beta-glucosidase, activity at a temperature between 30° C. and 35° C. compared with the beta-glucosidase activity of a 100B11 polypeptide comprising the amino acid sequence of SEQ ID NO: 5.

4. The variant polypeptide of claim 3, wherein the beta-glucosidase activity of the variant polypeptide is enhanced by at east 10% at a temperature between 30° C. and 35° C. compared with the beta-glucosidase activity of the 100B11 polypeptide comprising the amino acid sequence of SEQ ID NO: 5.

5. A purified or isolated nucleic acid, Wherein the nucleic acid encodes the variant polypeptide of claim 1.

6. The nucleic acid of claim 5, wherein the nucleic acid comprises the nucleic acid sequence of SEQ ID NO: 2.

7. A vector comprising the nucleic acid of claim 5.

8. An isolated host cell comprising the variant polypeptide of claim 1.

9. The isolated host cell of claim 8, which is selected from the group consisting of *Trichoderma, Aspergillus, Neurospora, Humicola, Penicillium, Fusarium, Thermomonospora, Myceliophthora, Chrysosporium, Bacillus, Pseudomonas, Escherichia, Clostridium, Cellulomonas, Streptomyces, Yarrowia, Pichia* and *Saccharomyces*.

10. The isolated host cell of claim 8, which is selected from the group consisting of *Trichoderma reesei, Trichoderma viridae, Trichoderma koningii, Aspergillus niger, Aspergillus nidulans, Aspergillus wentii, Aspergillus oryzae, Aspergillus phoenicis, Neurospora crassa, Humicola grisae, Myceliophthora thermopila, Chrysosporium lucknowense, Penicillium pinophilum, Penicillium oxalicum, Escherichia coli, Clostridium acetobutylicum, Clostridium saccharolyticum, Clostridium benjerinckii, Clostridium butylicum, Pichia pastoris, Yarrowia lipolityca, Saccharomyces cerevisiae*, and mixtures thereof.

11. The isolated host cell of claim 9, which is of the species *Trichoderma reesei*.

12. The isolated host cell of claim 9, which is of the species *Saccharomyces cerevisiae*.

13. A method for hydrolyzing beta-oligosaccharides, comprising contacting the beta-oligosaccharides with the variant polypeptide of claim 1 to thereby hydrolyze the beta-oligosaccharides.

14. A method for hydrolyzing cellobiose to glucose comprising contacting the cellobiose with the variant polypeptide of claim 1 to thereby hydrolyze the cellobiose to glucose.

15. An enzymatic composition which acts on lignocellulosic biomass, said enzymatic composition comprising the variant polypeptide of claim 1.

16. A process for producing a biofuel from lignocellulosic biomass, comprising:
    suspending, in an aqueous phase, a material to be hydrolyzed, wherein the material comprises lignocellulosic biomass;

contacting the material to be hydrolyzed with the enzymatic composition of claim 15 to hydrolyze the lignocellulosic biomass and to produce a hydrolysate containing glucose;
fermenting the glucose of the hydrolysate to produce a fermentation must comprising a biofuel; and
separating the biofuel from the fermentation must,
wherein the steps of hydrolyzing the lignocellulosic biomass and fermenting the glucose are carried out simultaneously.

* * * * *